(12) United States Patent
Parlato et al.

(10) Patent No.: US 12,127,749 B1
(45) Date of Patent: Oct. 29, 2024

(54) CEMENT REMOVAL BLADE FOR OSTEOTOME

(71) Applicant: HENRY SCHEIN, INC., Melville, NY (US)

(72) Inventors: Brian David Parlato, Hillsborough, NJ (US); Alfred Anthony Litwak, Keyport, NJ (US)

(73) Assignee: Henry Schein, Inc., Melville, NY (US)

( * ) Notice: Subject to any disclaimer, the term of this patent is extended or adjusted under 35 U.S.C. 154(b) by 458 days.

(21) Appl. No.: 17/699,831

(22) Filed: Mar. 21, 2022

Related U.S. Application Data

(63) Continuation-in-part of application No. 16/826,392, filed on Mar. 23, 2020, now Pat. No. 11,364,038, which is a continuation-in-part of application No. 15/369,839, filed on Dec. 5, 2016, now Pat. No. 10,595,879.

(60) Provisional application No. 63/164,915, filed on Mar. 23, 2021.

(51) Int. Cl.
*A61B 17/16* (2006.01)

(52) U.S. Cl.
CPC ...... *A61B 17/1624* (2013.01); *A61B 17/1604* (2013.01)

(58) Field of Classification Search
CPC ... A61B 17/16; A61B 17/1604; A61B 17/162; A61B 17/1626; A61B 17/1628; A61B 17/1633; A61B 17/1635; A61B 17/164; A61B 17/1642; A61B 17/1655; A61B 17/1657; A61B 17/1659; A61B 17/1662–1693; A61B 17/1695

USPC .......................................................... 606/84
See application file for complete search history.

(56) References Cited

U.S. PATENT DOCUMENTS

| | | | |
|---|---|---|---|
| 2,550,347 A | | 4/1951 | Gruber |
| 4,036,236 A | | 7/1977 | Rhodes, Jr. |
| 4,150,675 A | * | 4/1979 | Comparetto ....... A61B 17/1604 30/316 |
| 4,584,999 A | | 4/1986 | Arnegger |
| 4,600,005 A | * | 7/1986 | Hendel ................... B26D 3/06 30/167 |
| 4,617,930 A | | 10/1986 | Saunders |
| 4,768,504 A | | 9/1988 | Ender |
| 5,095,875 A | | 3/1992 | Morris |
| 5,147,364 A | * | 9/1992 | Comparetto ........... A61B 17/15 606/85 |
| 5,178,626 A | | 1/1993 | Pappas |
| D342,313 S | * | 12/1993 | Hood ........................... D24/146 |

(Continued)

OTHER PUBLICATIONS

American Educational Stainless Steel Pick Scoop, American Education Products.

*Primary Examiner* — Eric S Gibson
(74) *Attorney, Agent, or Firm* — Perilla Knox & Hildebrandt LLP

(57) ABSTRACT

An osteotome blade that is optimized for cutting and removal of bone cement such as from an intramedullary canal during revision surgery. The blade may have a body and a tip, wherein the body cross-section and tip are trough-shaped and the tip has a swept-back configuration. Further away from the cutting region, the blade may have a transition region and a hub suitable to be grasped in a power tool. There may also be provided a scoring blade, and a method may comprise scoring grooves into bone cement using the scoring blade, followed by removal of bone cement using the cement removal blade.

20 Claims, 21 Drawing Sheets

(56) References Cited

U.S. PATENT DOCUMENTS

| | | | |
|---|---|---|---|
| D344,801 S * | 3/1994 | Hughes | D24/146 |
| 5,507,763 A | 4/1996 | Petersen et al. | |
| 5,676,680 A | 10/1997 | Lim | |
| 5,735,855 A * | 4/1998 | Bradley | A61B 17/1604 606/86 R |
| 6,110,175 A * | 8/2000 | Scholl | A61B 17/1604 606/79 |
| 6,187,012 B1 * | 2/2001 | Masini | A61F 2/4607 606/99 |
| 6,485,495 B1 * | 11/2002 | Jenkinson | A61B 17/32 606/167 |
| 6,610,066 B2 | 8/2003 | Dinger et al. | |
| 6,790,211 B1 * | 9/2004 | McPherson | A61F 2/4607 606/169 |
| 6,896,679 B2 | 5/2005 | Danger et al. | |
| 7,833,241 B2 | 11/2010 | Gant | |
| 7,850,694 B2 | 12/2010 | Raus | |
| 8,100,912 B2 | 1/2012 | Marietta | |
| 8,328,813 B2 | 12/2012 | Raus | |
| 8,372,077 B2 * | 2/2013 | Taylor | A61F 2/4607 606/82 |
| 8,545,501 B2 * | 10/2013 | Wong | A61B 17/56 606/86 R |
| 8,672,943 B2 | 3/2014 | Fisher et al. | |
| 8,734,450 B2 * | 5/2014 | Landon | A61B 17/142 30/337 |
| 8,852,221 B2 | 10/2014 | Boykin et al. | |
| 8,858,559 B2 * | 10/2014 | Milburn | A61B 17/14 606/177 |
| 8,888,783 B2 * | 11/2014 | Young | A61B 17/1637 606/177 |
| 8,920,424 B2 * | 12/2014 | Boykin | B27B 33/02 606/82 |
| 8,966,772 B2 | 3/2015 | Legrand et al. | |
| 9,138,242 B2 | 9/2015 | Lewis et al. | |
| 9,198,776 B2 * | 12/2015 | Young | A61F 2/4607 |
| 9,242,361 B2 | 1/2016 | Kaye, Jr. et al. | |
| 9,332,996 B2 | 5/2016 | Estes | |
| 9,848,900 B2 * | 12/2017 | Witt | A61B 17/320068 |
| 9,867,628 B2 * | 1/2018 | Macke | A61B 17/1742 |
| 9,867,647 B2 | 1/2018 | Mirza | |
| 10,548,618 B2 | 2/2020 | Palmatier et al. | |
| 10,589,410 B2 | 3/2020 | Aho | |
| 10,595,879 B1 * | 3/2020 | Litwak | A61B 17/142 |
| 10,624,651 B2 | 4/2020 | Aman et al. | |
| 10,959,738 B2 | 3/2021 | Sweitzer | |
| 10,966,842 B2 | 4/2021 | Kulper et al. | |
| 11,039,936 B2 | 6/2021 | Paul | |
| 11,116,525 B2 | 9/2021 | Wright | |
| 11,229,497 B2 | 1/2022 | Schwartzbauer | |
| 11,364,038 B1 * | 6/2022 | Litwak | A61B 17/1668 |
| 2004/0098000 A1 * | 5/2004 | Kleinwaechter | B23D 61/123 D24/146 |
| 2007/0123893 A1 * | 5/2007 | O'Donoghue | A61B 17/142 606/82 |
| 2010/0057118 A1 | 3/2010 | Dietz | |
| 2011/0034932 A1 * | 2/2011 | Paulos | A61B 17/16 606/84 |
| 2011/0288555 A1 * | 11/2011 | Szanto | A61B 17/1637 606/84 |
| 2012/0144971 A1 | 6/2012 | Bohne | |
| 2014/0090537 A1 | 4/2014 | Campbell et al. | |
| 2014/0163558 A1 | 6/2014 | Cosgrove et al. | |
| 2014/0316415 A1 * | 10/2014 | Young | A61B 17/16 606/84 |
| 2020/0121474 A1 | 4/2020 | Pendleton et al. | |
| 2021/0068851 A1 | 3/2021 | Sweitzer | |
| 2021/0282939 A1 | 9/2021 | Wright | |
| 2021/0338297 A1 | 11/2021 | Young et al. | |
| 2022/0323134 A1 | 10/2022 | Lyon et al. | |

\* cited by examiner

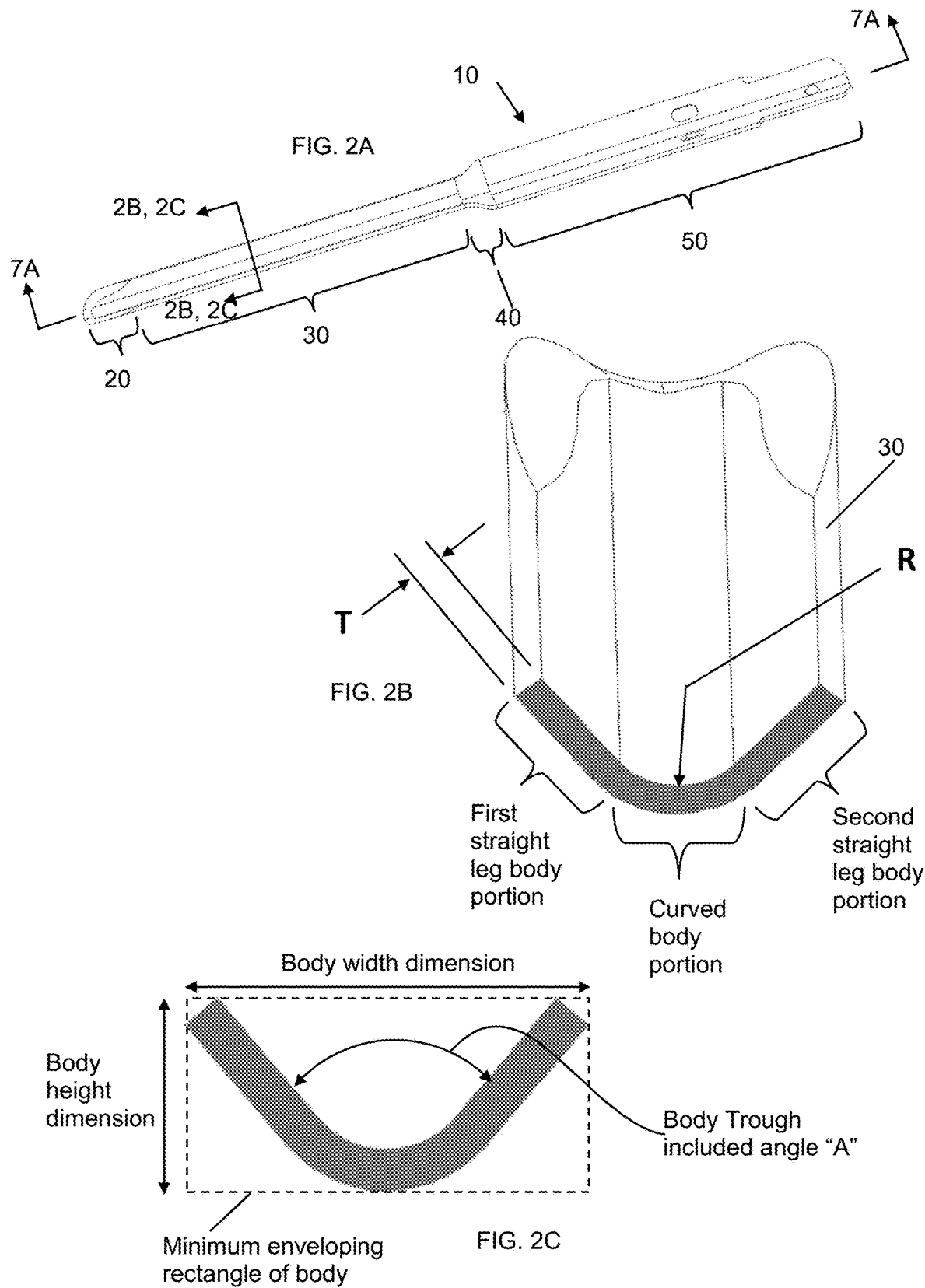

Round  Hexagonal  Pointed
or Octagonal
 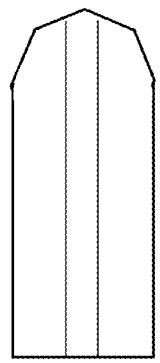 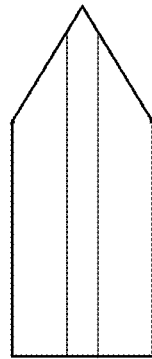
FIG. 5A   FIG. 5B   FIG. 5C
Flat or Round   Flat Pointed   Round Pointed
with Concave
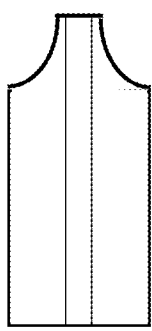 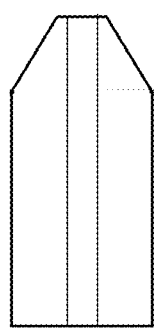 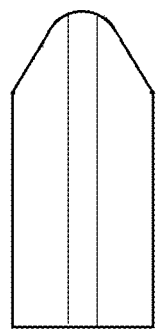
FIG. 5D   FIG. 5E   FIG. 5F $R_T < .010$ Inch Bevel Angle "E"

Center Grind Edge
Top Grind Edge
Bottom Grind Edge
FIG. 7B Round Edge   Triangular Edge   V- Straight Edge   Concave Edge   V- Slanted Edge   Flat Edge

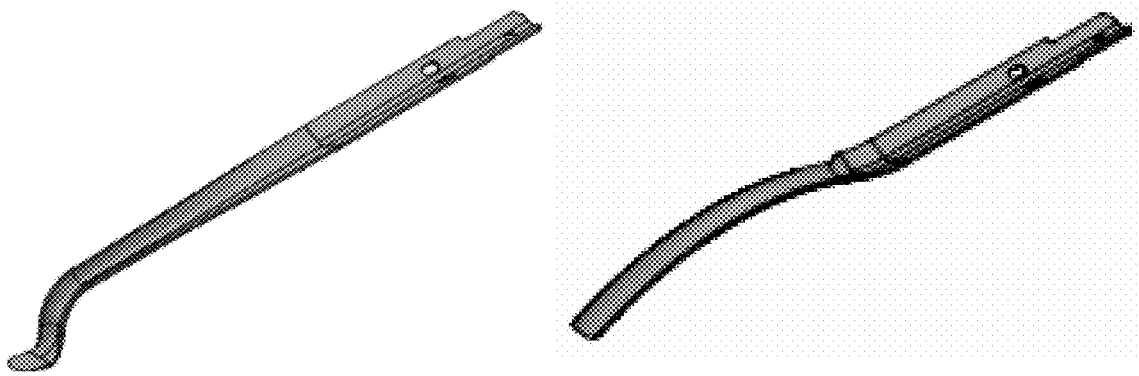
FIG. 15A        FIG. 15B
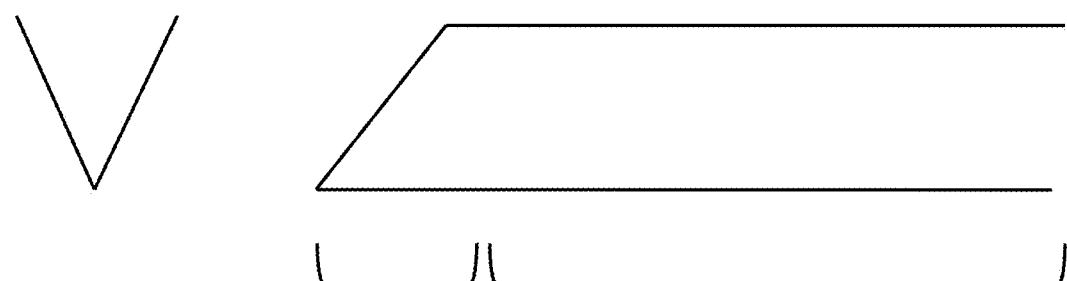
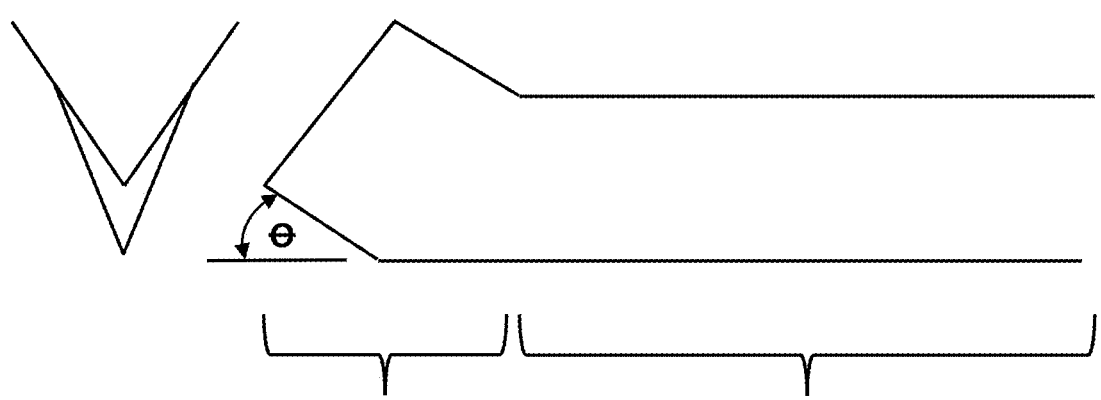
FIG. 16

FIG. 17D
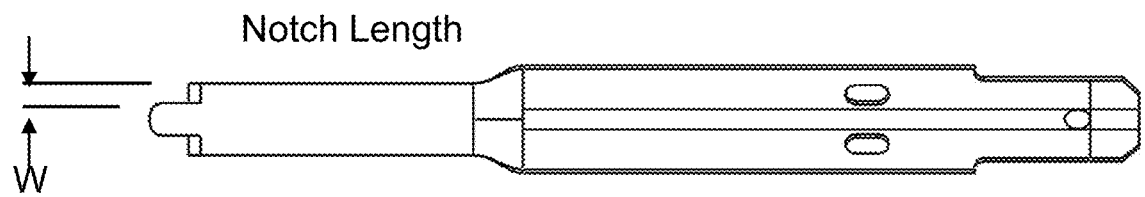
FIG. 17E
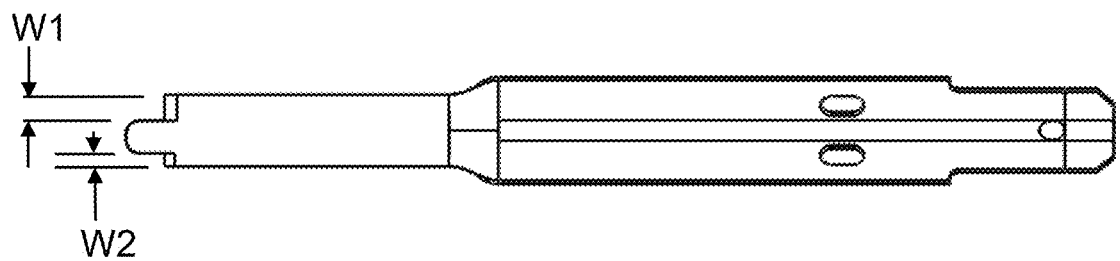
FIG. 17F
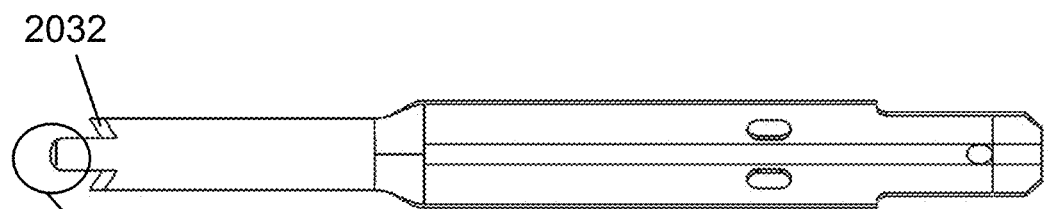
FIG. 17G
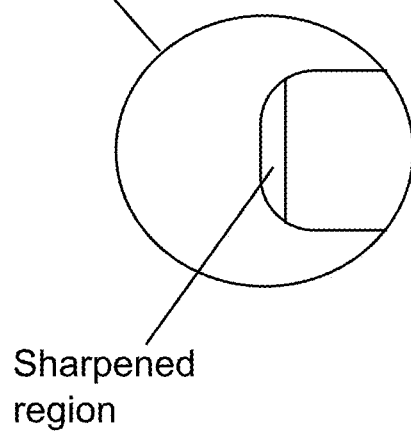

Axial Scoring Cut
Bone Cement
Bone

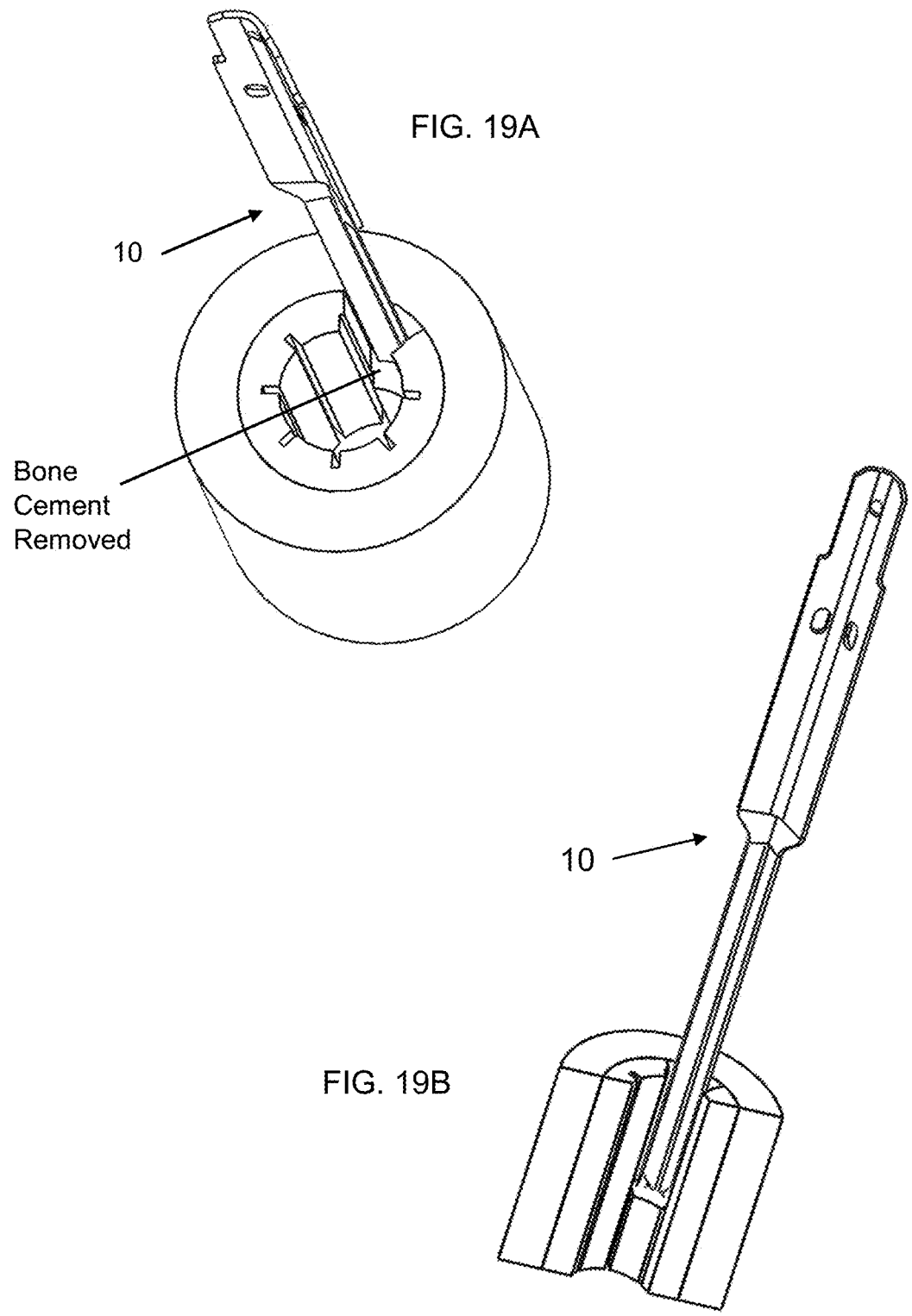

CEMENT REMOVAL BLADE FOR OSTEOTOME

CROSS-REFERENCE TO RELATED APPLICATION

This patent application is a Continuation-in-Part patent application of U.S. Ser. No. 16/826,392, filed Mar. 23, 2020, which is a Continuation-in-Part of U.S. Ser. No. 15/369,839, filed Dec. 5, 2016, now U.S. Pat. No. 10,595,879. This patent application claims the benefit of U.S. provisional patent application Ser. No. 63/164,915 filed Mar. 23, 2021. Reference is also made to U.S. Ser. No. 17/402,511, filed Aug. 14, 2021, which claims the benefit of U.S. Ser. No. 63/066,089, filed Aug. 14, 2020. All of these are incorporated herein by reference in their entireties.

FIELD OF THE INVENTION

Embodiments of the invention pertain to cutting tools and orthopedic surgery.

BACKGROUND OF THE INVENTION

In orthopedic surgery it has historically been a difficult task to cut through bone cement that already exists in the body of the patient, such as when performing a revision of a previous surgery at the same site. Bone cement typically comprises Polymethyl Methacrylate (PMMA) and is a very tough material that is not easily cut.

One method currently used to remove bone cement is the manual osteotome, or bone chisel, which is used in combination with a hammer to manually chisel out the bone cement piece by piece. This is a very slow and laborious process.

Another method is an ultrasonic device (for example Orthofix's Oscar™ system) fitted with various blades. The frequency of the blade vibrations is matched to the natural frequency of the bone cement. This produces heat which causes the softening and/or melting of the bone cement, which allows the cement to be scooped and scraped out of bone cavities and off of bone surfaces. This is a slow and messy process that also produces noxious odors.

There are also various types of hooks, scrapers, and reamers that are used to try to remove bone cement. None of these methods is fast or easy to use. Accordingly, improvements are still desirable, especially with a view toward reducing the duration of surgery.

SUMMARY OF THE INVENTION

In an embodiment of the invention, there may be provided a blade for cutting, the blade comprising: a tip, the tip having a tip thickness measured perpendicular to a local surface of the blade; and a body, proceeding proximally from the tip, the body having a body width dimension; wherein the body and the tip both extend generally along a proximal-distal direction, wherein the tip is trough-shaped having a tip concave surface and an opposed tip convex surface, wherein the tip has a tip cross-section, taken perpendicular to the proximal-distal direction, wherein, the tip cross-section has a concave surface that has, at some location, a tip internal radius of curvature that is a smallest radius of curvature of the concave surface, wherein the tip cross-section can be enveloped by a minimum tip enveloping rectangle that is a smallest rectangle that can enclose the tip cross-section, wherein the minimum tip enveloping rectangle has a tip section width dimension and a tip section height dimension and has a tip aspect ratio that is a ratio of the tip section width dimension to the tip section height dimension, wherein the tip aspect ratio ranges from 1.0 to 3.5, wherein the tip internal radius of curvature is between 2% and 40% of the body width dimension, wherein the tip internal radius of curvature is approximately 0.05 to 6.25 times the tip thickness, wherein when viewed from above the concave surface, the tip has a swept-back configuration, and wherein the tip has a distal edge having a suitable sharpness and hardness to cut a material of interest. Furthermore, the body may be continuous with a transition region and a hub that is suitable to be gripped in a chuck of a power instrument.

In an embodiment of the invention, there may be provided a method of cutting bone cement comprising providing the described blade and repeatedly striking the bone cement suitably to cut it.

In an embodiment of the invention, there may be provided a blade for use in cutting, the blade comprising: a guidance portion; a cutting portion that is continuous with the guidance portion; a transition portion that is continuous with the cutting portion; and a gripping portion that is continuous with the transition portion, wherein the blade has a longitudinal axis, wherein the cutting portion is planar having a cutting portion planar surface facing in an upward direction and has at least one cutting edge that is adapted for cutting, wherein the gripping portion has an upward-facing surface facing generally in the upward direction and the upward-facing surface does not entirely lie in a single plane, and wherein the transition portion has a three-dimensional surface transitioning between the cutting portion and the gripping portion, wherein the guidance portion comprises edges that are less sharp than the cutting edge of the cutting portion.

In an embodiment of the invention, there may be provided a method of cutting bone cement comprising providing the described scoring blade and repeatedly striking the bone cement suitably to cut an axial score into the bone cement. In an embodiment, such scoring may be followed by cutting the material remaining between score marks using a different blade that is suited for cutting or chipping away the remaining bone cement.

BRIEF DESCRIPTION OF THE ILLUSTRATIONS

FIG. 1A is an illustration of a typical femoral component of a hip replacement, implanted in a femur. FIG. 1B shows the femoral component removed from the femur, also showing bone cement remaining in the intramedullary canal of the femur. FIG. 1C shows bone cement being removed from the intramedullary canal using an embodiment of the invention.

FIG. 2A is a three-dimensional perspective view of a blade of an embodiment of the invention. FIG. 2B is a sectional view of FIG. 2A. FIG. 2C is a further sectional view of FIG. 2A.

FIGS. 5A-5F show various possible shapes of the tip of the blade.

Figure 6A:
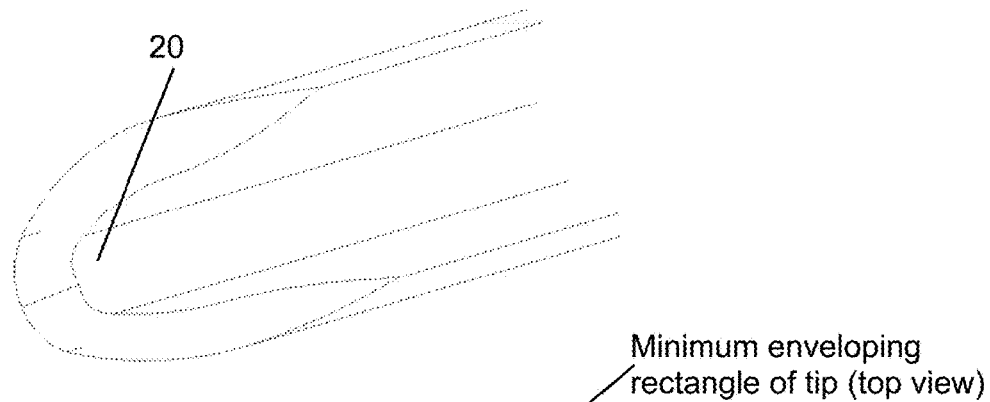
Figure 6B:
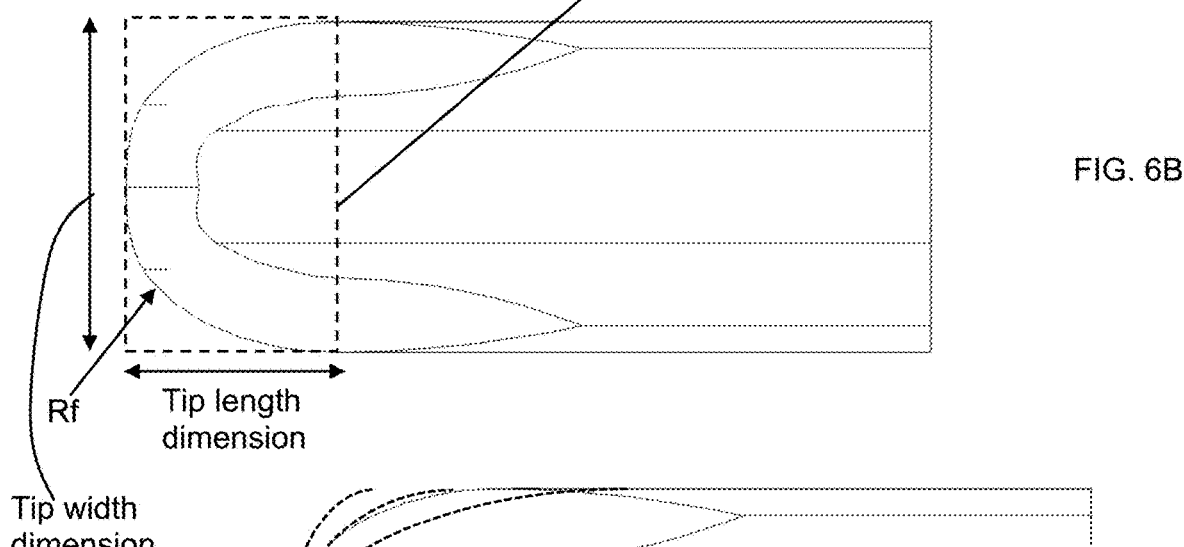

FIG. 6A shows a three-dimensional perspective view of the tip and a portion of the body of a blade of an embodiment of the invention. FIG. 6B is a corresponding top view. FIG.

6C is FIG. 6B with, superimposed, a semicircle and two semi-ellipses. FIGS. 6D-6H show various cross-sections through the tip.

Figure 7A:
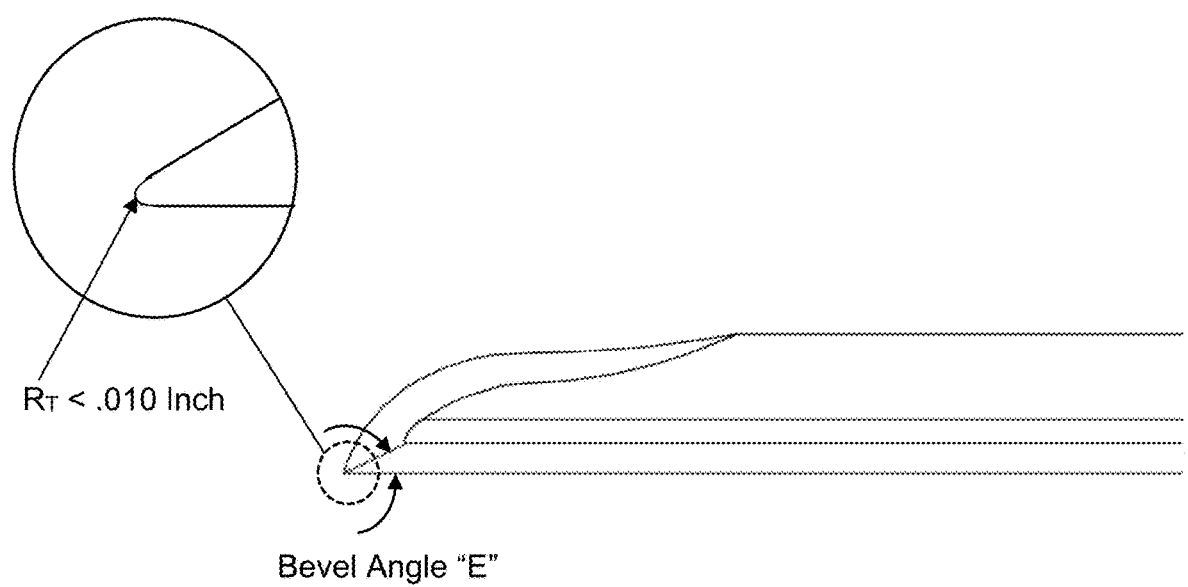

FIG. 7A is a cross-section of FIG. 2A showing the bevel angle of the cutting edge of the blade. FIG. 7B illustrates possible locations of grinding of the cutting edge of the blade.

Figure 8A:
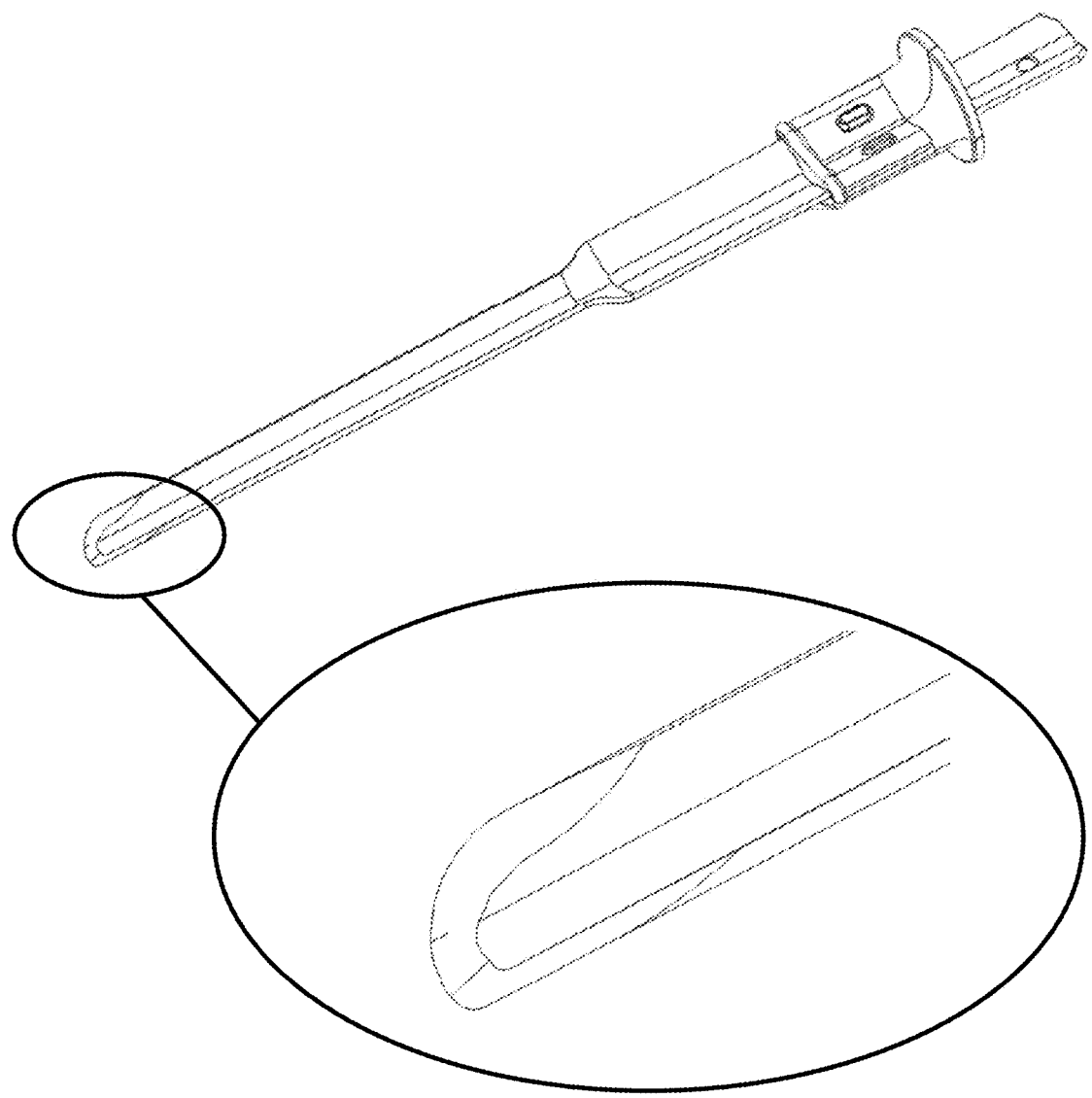
Figure 8B:
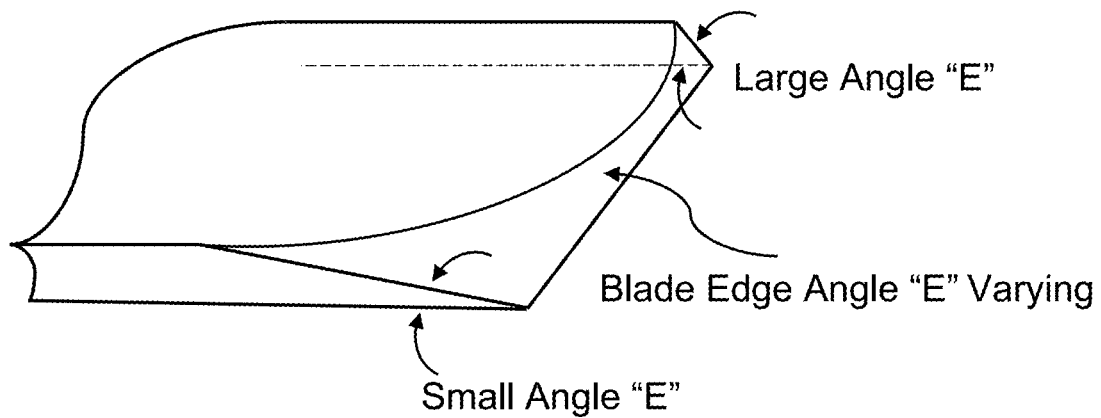
Figure 8C:
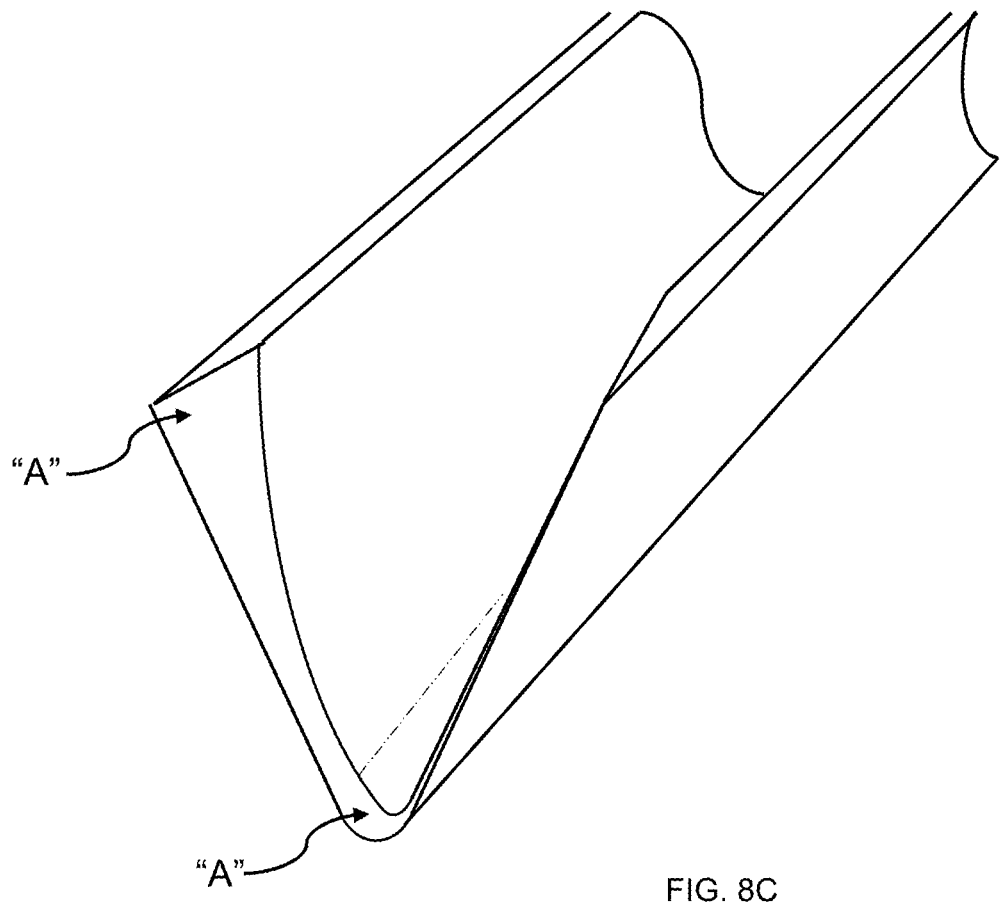

FIG. 8A illustrates the blade and its tip, particularly the tapering of the region that is ground or sharpened. FIGS. 8B and 8C illustrate possible details of the region that is ground.

Figures 9A, 9B:
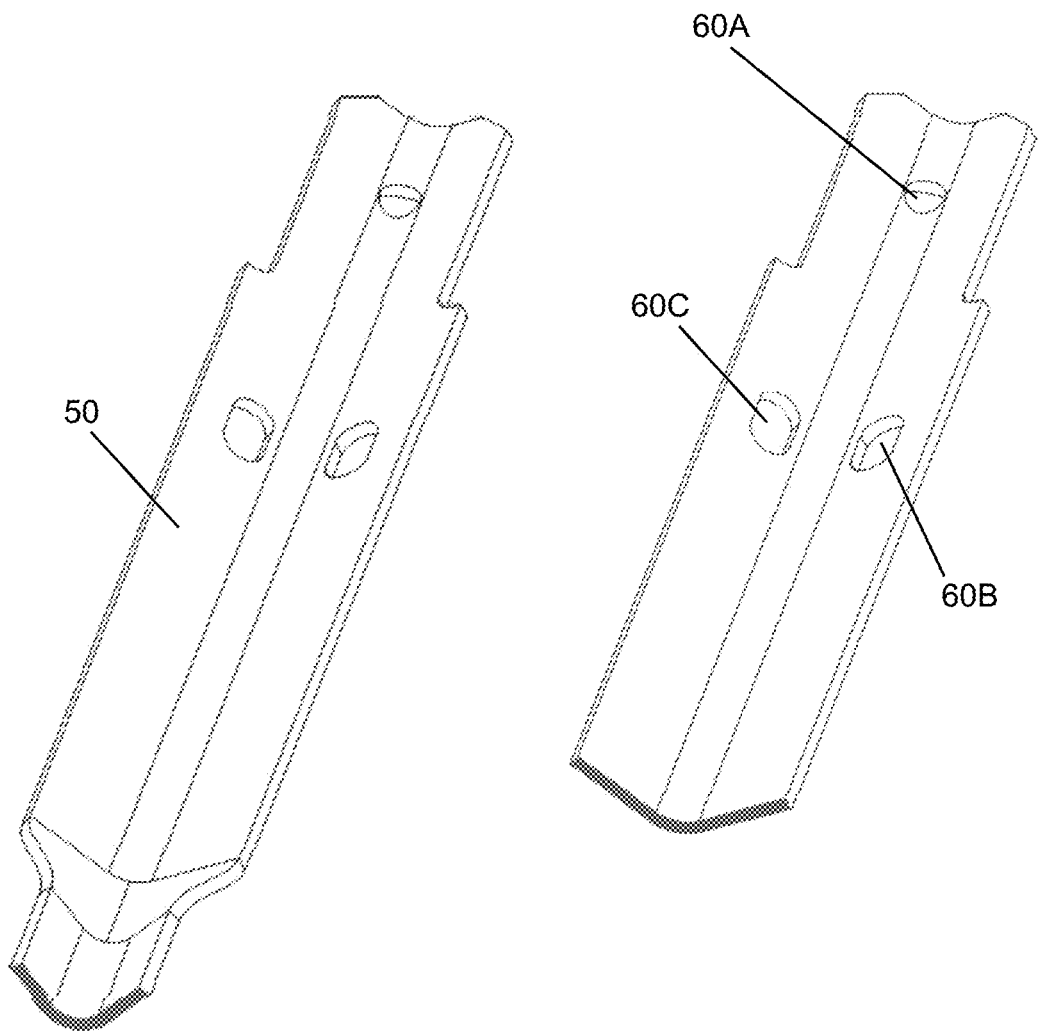

FIG. 9A illustrates the hub of the blade. FIG. 9B illustrates a cross-section of the hub of FIG. 9A.

Figure 10A:
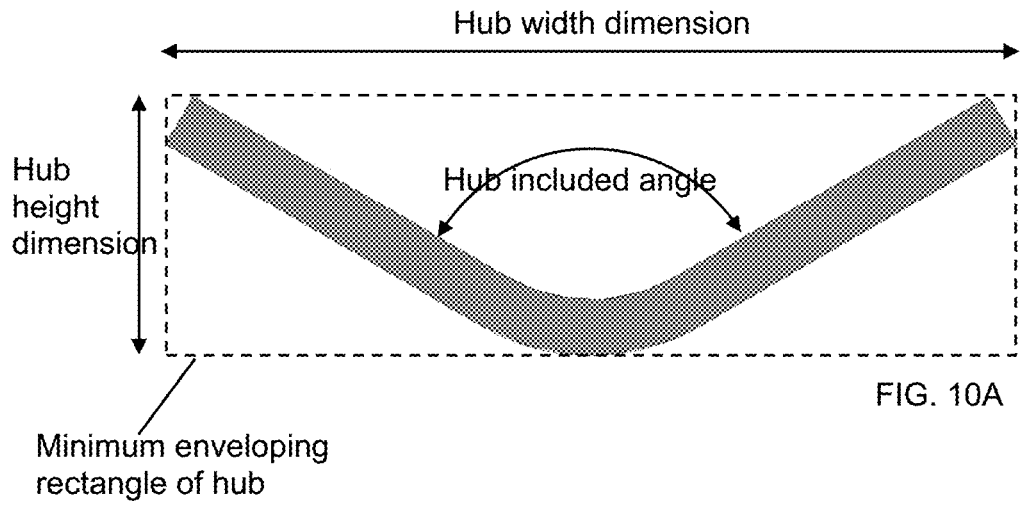
Figure 10B:
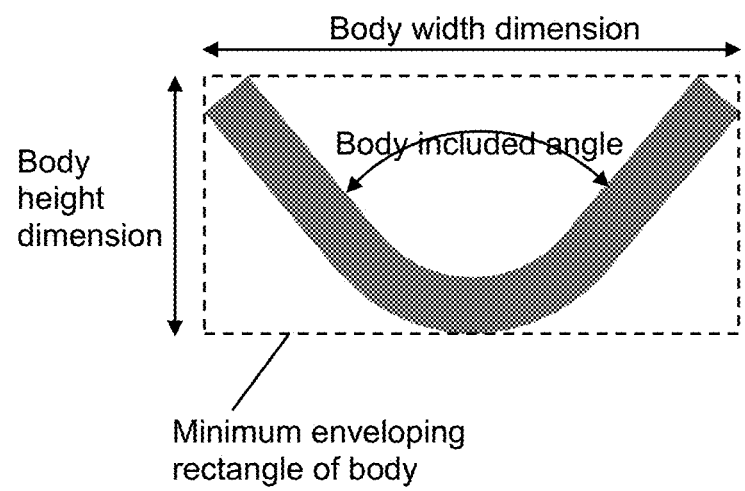

FIG. 10A is a cross-section of the hub illustrating an included angle and the minimum enveloping rectangle. FIG. 10B (like FIG. 2C) is a sectional view of the body of the blade.

Figure 11:
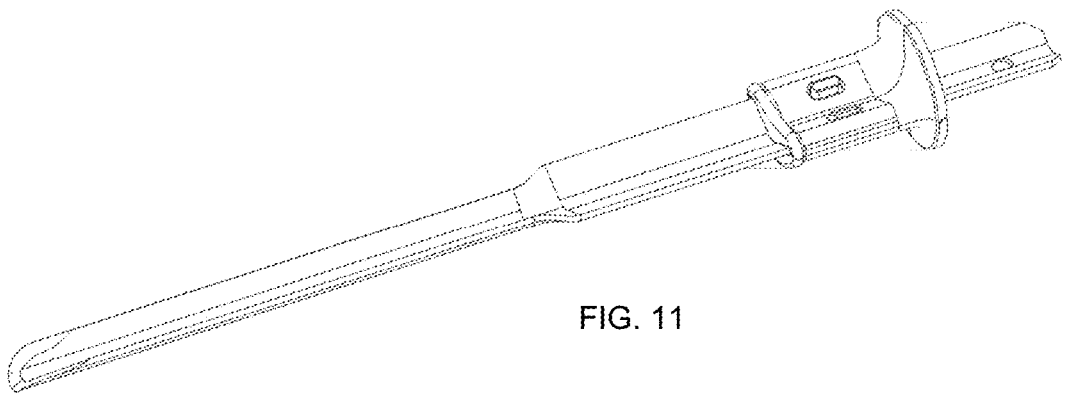

FIG. 11 shows the blade together with its splash guard.

Figure 12:
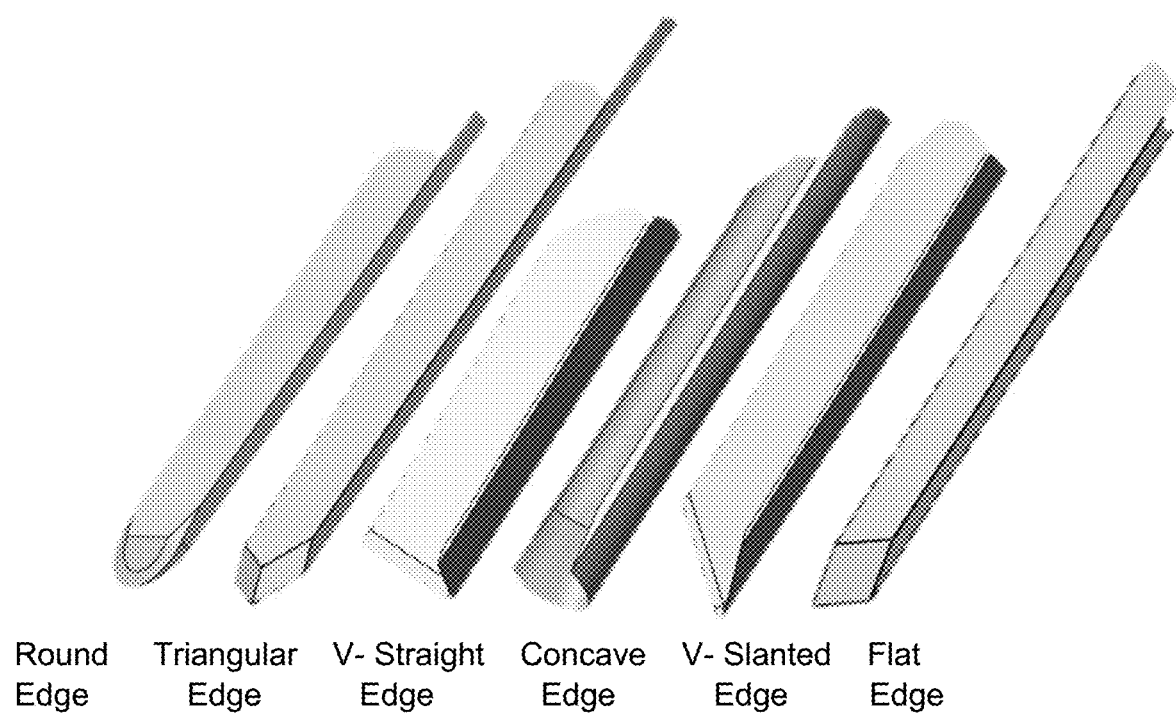

FIG. 12 illustrates various shapes of the tip of the blade that were tested during the configuration survey portion of the testing.

Figure 13:
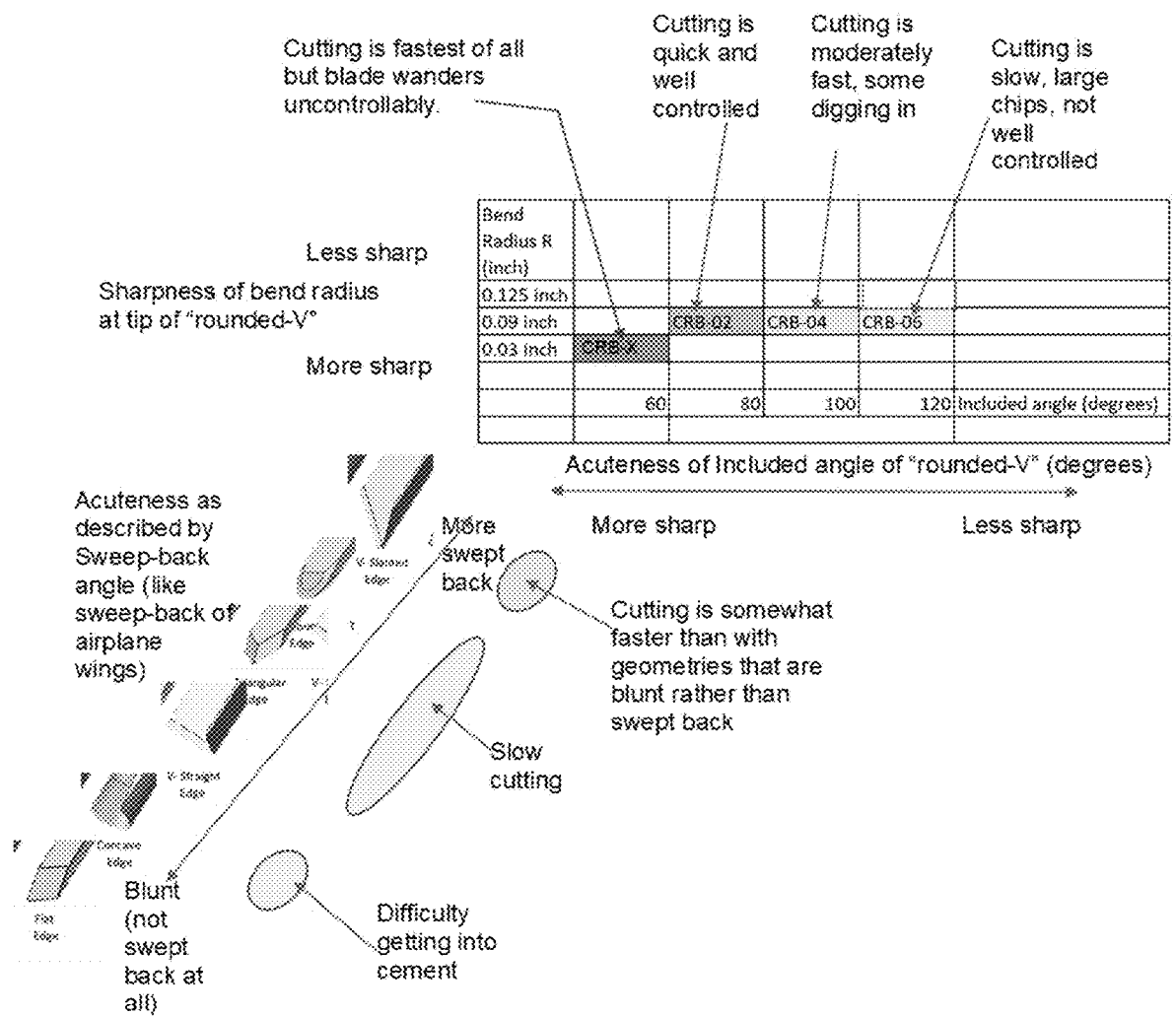

FIG. 13 is a pictorial summary of the various stages of testing along with trends observed.

Figure 14:
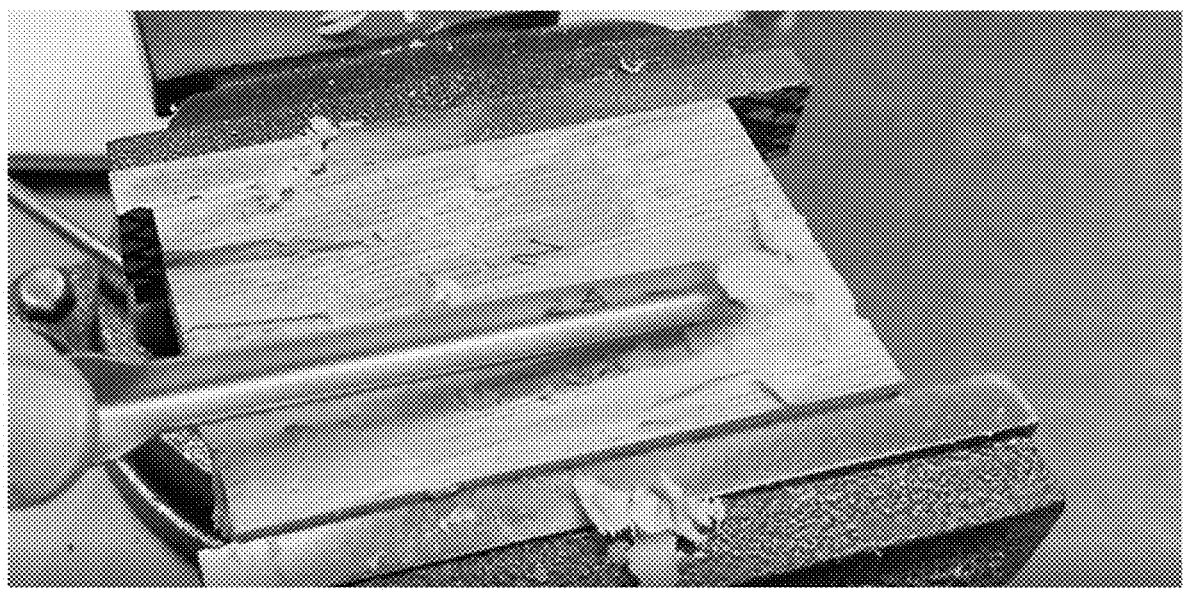

FIG. 14 shows a blade, of an embodiment of the invention, being tested.

FIGS. 15A and 15B show embodiments of the invention in which the body of the blade has a longitudinal path that is other than straight.

FIG. 16 shows an embodiment of the invention in which the tip includes a bend or angle.

Figure 17A:
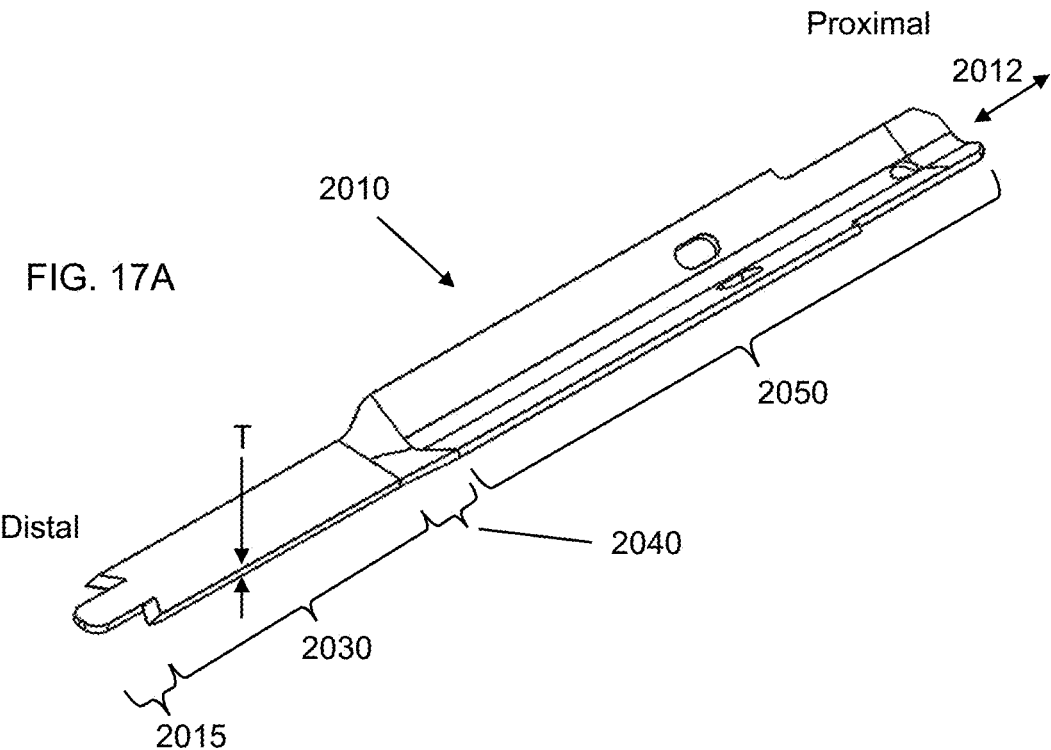
Figure 17B:
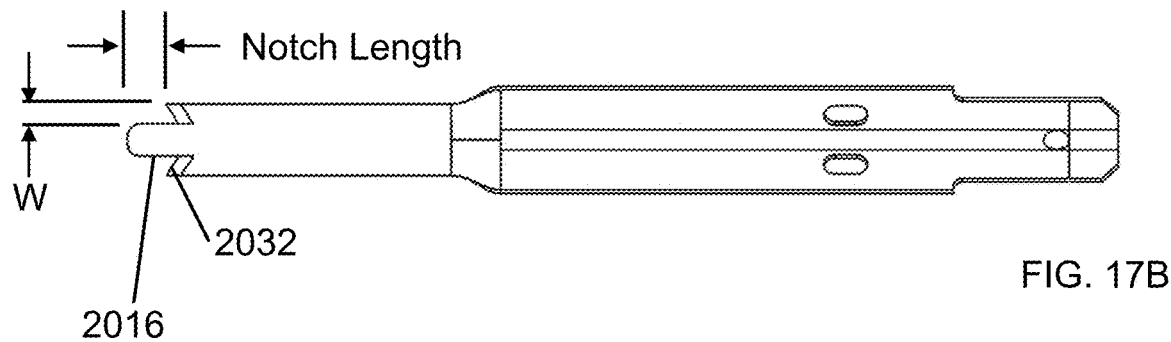
Figure 17C:
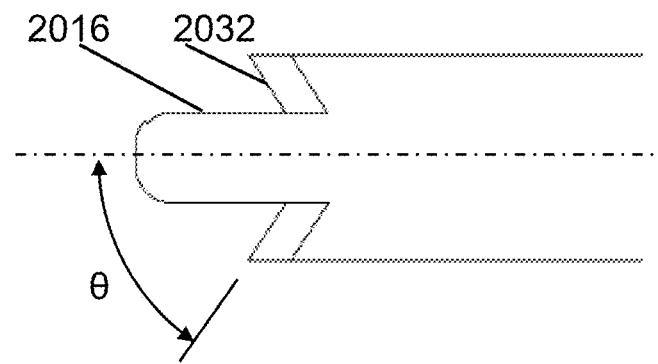

FIG. 17A is a three-dimensional perspective view of a scoring blade. FIG. 17B is a top view of the same blade. FIG. 17C illustrates that the cutting edge of the scoring blade forming a defined angle with respect to the long axis of the blade 2010. FIG. 17D is a side view of the same blade. FIG. 17E shows a blade in which the guidance region is symmetrically located. FIG. 17F shows a blade in which the guidance region is offset from the longitudinal axis of the blade. FIG. 17G shows a scoring blade in which the guidance region has a tip that is sharpened.

Figure 18A:
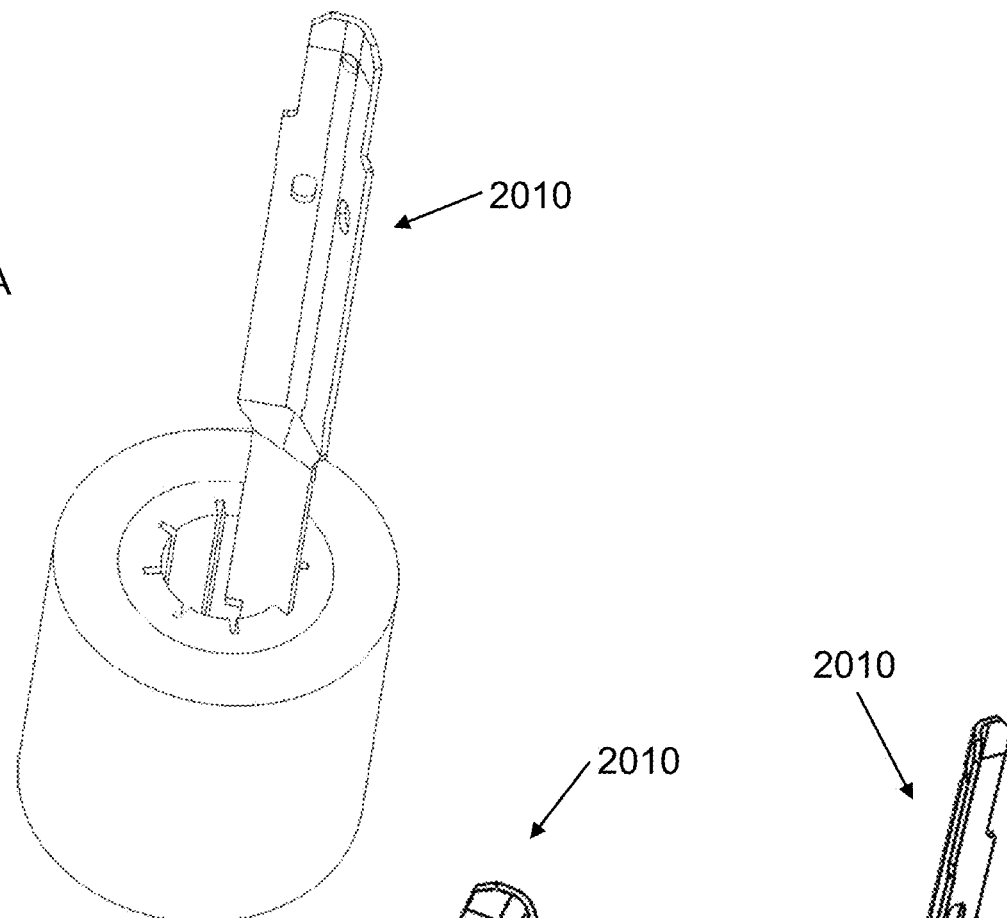
Figure 18B:
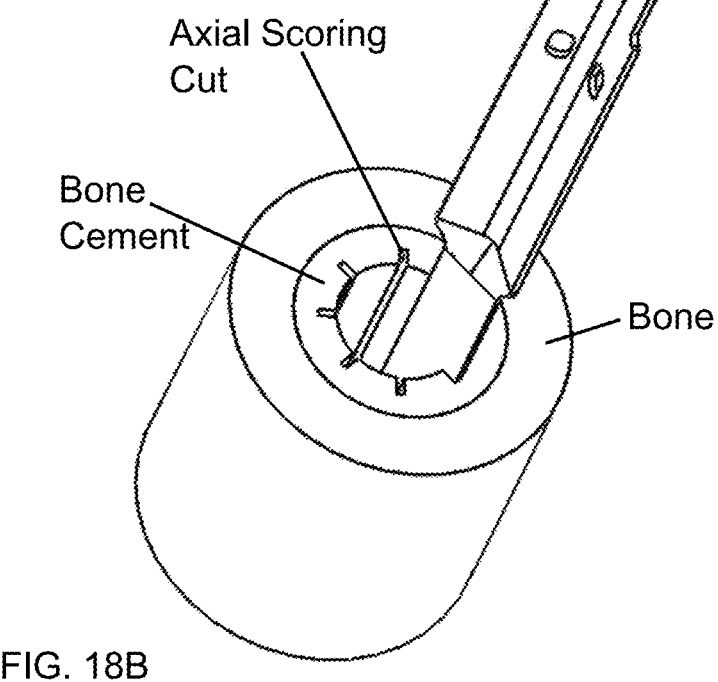
Figure 18C:
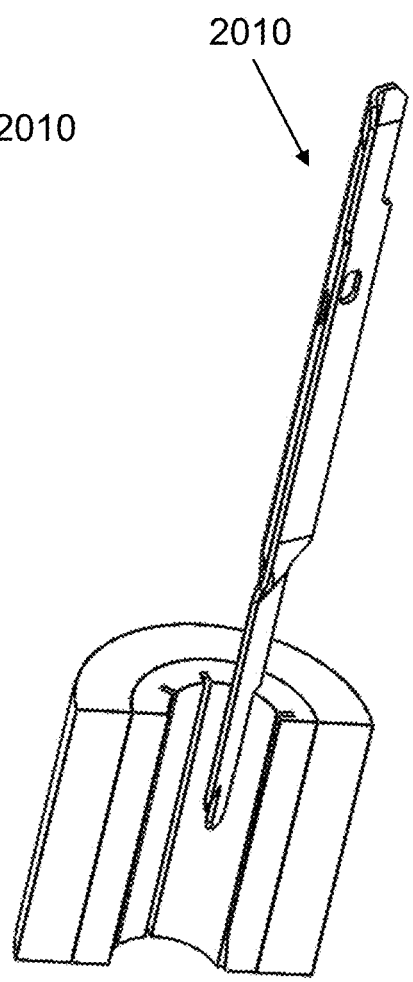

FIG. 18A shows the use of the axial scoring blade at the beginning of a scoring cut. FIG. 18B shows the use of the axial scoring blade during a scoring cut. FIG. 18C is a sectional view of FIG. 18B.

FIG. 19A shows the use of the Cement Removal Blade after the creation of scoring cuts. FIG. 19B is a sectional view of FIG. 19A.

DETAILED DESCRIPTION OF THE INVENTION

In an embodiment of the invention, there is provided a blade 10 that is suitable to work with a powered handpiece or instrument such as an osteotome that actuates the blade 10 forward, or back and forth many times per second. The power stroke on each actuation, which is typically the forward direction, is the direction that causes the blade 10 to cut. In such usage, each actuation of the blade 10 causes an impact to the bone cement or other material with which the blade 10 is in contact, suitably to cut or chip the bone cement or other material.

Figure 1A:
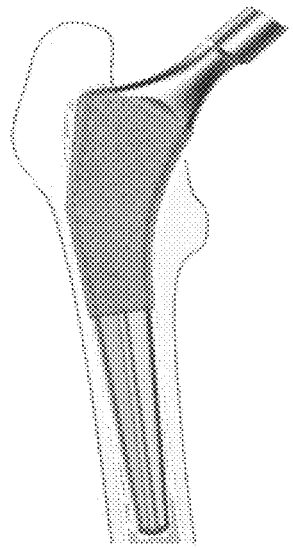
Figure 1B:
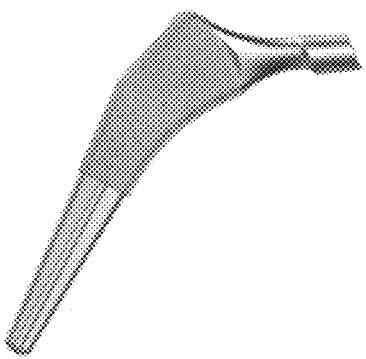
Figure 1C:
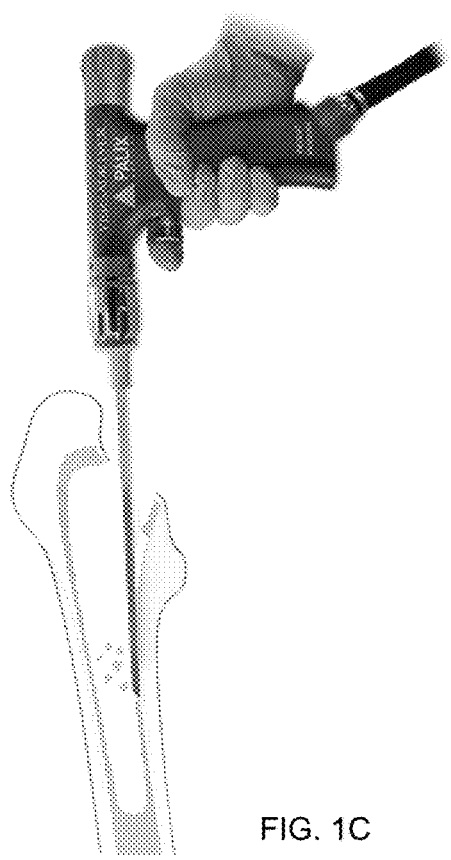

In embodiments of the invention, the blade 10 may be suitable to be used in an intramedullary canal of a bone, such as the intramedullary canal of a femur, to remove bone cement that had been placed there during an earlier surgery. This is illustrated in FIGS. 1A, 1B and 1C. FIG. 1A a typical femoral component of a hip replacement, as it is normally implanted in a femur. FIG. 1B shows the femoral component removed from the femur, as during revision surgery. FIG. 1B also shows bone cement remaining in the intramedullary canal of the femur. FIG. 1C shows bone cement being removed from the intramedullary canal using an embodiment of the invention.

The intermedullary canal of an adult human femur is usually less than 25 mm inside diameter in the region of the femur that is occupied by the shaft of a femoral implant for hip replacement. Therefore, in order to remove bone cement, cutting blades need to be able work in space-limited openings that are of a generally cylindrical shape, often in spaces that have an inside diameter of approximately 12-18 mm. So, the width of blade 10 may be such as to be capable of fitting in spaces of those dimensions, while also being able to effectively cut and remove material such as bone cement.

Referring now to FIG. 2A, there is shown an overall view of a blade 10 of an embodiment of the invention. The blade 10 may have a longitudinal direction that is a proximal-distal direction. The blade 10 may comprise in sequence, a tip 20, a body 30, a transition region 40, and a hub 50. These components are listed proceeding in sequence from distal (farthest from the hub 50, closest to the patient) to proximal (the hub 50, closest to the user).

In general, the performance of the blade for cutting bone cement may be influenced by the following geometric parameters, which are discussed herein:

Blade Thickness T
Radius of curvature "R" at bottom or vertex of the trough
Body trough included Angle "A" of the trough, or, more generally, the aspect ratio of the minimum enveloping rectangle of the body
Sweep-back properties.
Tip shape frontal geometry in plan view, such as frontal radius Rf
Angle "E" (angle of the bevel at the cutting edge)
Cutting edge location relative to thickness of tip
Radius of Sharpness of the tip (Rt in FIG. 7A)

In regard to blade thickness of blade 10, the blade 10 may, as illustrated, have a blade thickness T, which may be substantially constant throughout the blade 10. Such construction may be consistent with manufacturing the blade starting from sheet material and later forming the blade into a three-dimensional shape such as by stamping or bending. The blade thickness T may be 0.042 inch, or more generally in the range of 0.010 inch to 0.125 inch. Alternatively, the blade thickness could be tapered or of varying thickness. The width of the blade 10 may be 0.2 inches to 1.0 inches.

Geometric Details of Trough of Body

Figure 3A:
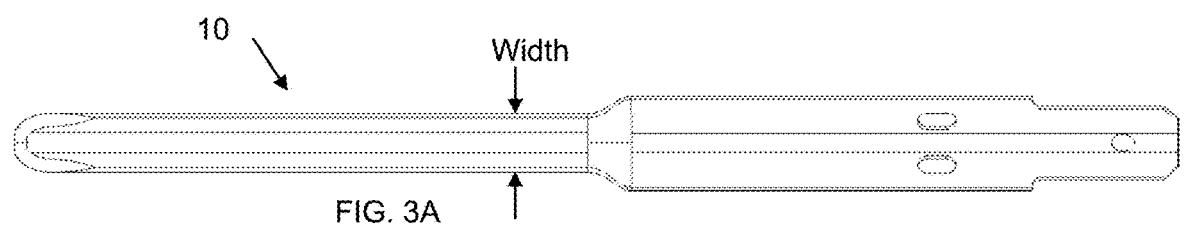
FIG. 3A is a top view of the blade of FIG. 2A.
Figure 3B:
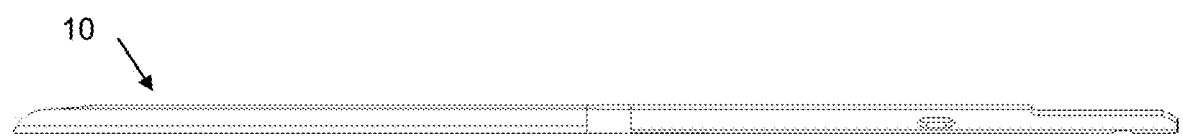
FIG. 3B is a side view of the same blade.

As illustrated in FIG. 2, in embodiments of the invention, the body 30 of the blade 10 may have a cross-sectional shape that is generally a trough shape having a concave (upward) surface and an opposed convex (downward) surface. In some embodiments, as illustrated in FIG. 3, the cross-sectional shape of the body may be a "rounded-V" shape with a rounded bottom as seen in FIG. 2A and enlarged in FIG. 2B. In such a situation, the cross-sectional shape may comprise, in succession, a first straight leg body portion, a curved body portion that is continuous with the first straight leg body portion, and a second straight leg body portion that is continuous with the curved body portion. This internal radius of curvature of the curved body portion can have desired relationships with other geometric parameters of the blade 10, as described elsewhere herein. The first and second straight leg body portions may define an included angle "A" (body trough included angle) between them. Exemplary values of the included angle are discussed elsewhere herein.

More generally, the body cross-section does not have to be exactly a rounded-V shape, but still it may be trough-shaped and have a concave surface. Even though a generalized shape might not have any straight segment, the shape still may have, at some location, a body internal radius "R" that is a minimum radius of curvature of the concave surface of the body cross-section. As before, this internal radius of curvature can have desired relationships with other geometric parameters of the blade 10, as described elsewhere herein.

Continuing in regard to this more generalized shape, the cross-section may be described by a minimum body enveloping rectangle that is the smallest rectangle that can enclose the body cross-section. This is illustrated in FIGS. 2C and 10B. As can be seen, the minimum body enveloping rectangle is tangent to the concave surface of the body at the underside of the body, and elsewhere the rectangle touches various corners of the edges of the body cross-section. The minimum body enveloping rectangle has a body width dimension and a body height dimension. From these two dimensions can be calculated a body aspect ratio that is a ratio of the body width dimension to the body height dimension. This aspect ratio can convey somewhat similar information as the included angle that is defined for a rounded-V cross-section, but the aspect ratio is applicable in generalized situations whether or not the cross-sectional shape comprises any straight-line segments. Exemplary values of this aspect ratio parameter are given elsewhere herein.

It can be noted that as illustrated, the tip 20 and the body 30 may have substantially identical cross-section, and one difference between the tip 20 and the body 30 lies in the external shape of the tip 20. In particular, the tip 20, when viewed in plan view, may have a contoured distal end, which signifies the absence of material. Also, an edge of the tip 20 may have a beveled or tapered sharp edge suitable for cutting. As shown in FIG. 7A, the tip radius of the cutting edge may be less than 0.01 inch. More generally, it is possible that the cross-sectional shape of the body 30 and the cross-sectional shape of the tip 20 of the blade 10 do not, in general, have to be the same as each other. For example, there could be differences in parameters such as angles, radii, and lengths of sides, for example.

In regard to trough radius, the trough radius "R" in FIG. 2B of the "rounded-V" portion of the blade 10, as measured at the inside (concave) surface of the bend, may be between 0.02 inches and 0.20 inches. This is believed to correspond to the best cutting action of the blade 10 on bone cement. More specifically, a typical dimensional value of that radius may be 0.03 inch or 0.09 inch. A further way of describing this may be that the ratio of trough radius to blade material thickness may be in the range of 0.15 to 6.0, or, more specifically, between 0.5 and 4.0. The body internal radius of curvature may be between approximately 0.05 to 6.25, or between 0.2 to 4, times the body thickness. The body internal radius of curvature may be between 2% and 40%, or between 5% and 25%, of the body width dimension.

In regard to trough included angle, the trough included angle "A" in FIG. 2C of the "rounded-V" tip cutting portion of the blade 10 may be between 40 and 140 degrees. This is believed to be the range of angles that provide good cutting action. A preferred value of the trough included angle would be approximately 80 degrees.

For situations in which the geometry is described by the aspect ratio of the minimum body enveloping rectangle, it is found that good cutting results are obtained with a body aspect ratio in the range of 1.0 to 3.5. Of course, the choice of a body aspect ratio or an included angle can also be influenced by the geometry of the intramedullary canal or other aspects of the surgical site for which use is intended.

Geometric Details of the Tip

The tip 20 may be the portion of the blade 10 that impacts the bone cement or other material at the surgical site and does the actual cutting. In embodiments of the invention, there may in general be some kind of tapering or reducing of dimensions at or near the tip, or sweeping-back, so that impact or compressive force carried by the body 30 of the blade 10 is applied to a working area that is smaller than the cross-sectional area of the body 30 itself.

Figure 4:
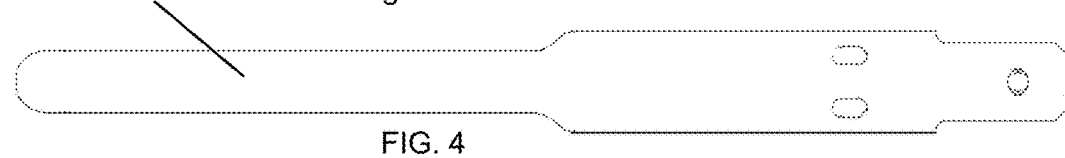
FIG. 4 is a layout of a flat shape that can be bent or formed into the blade of FIG. 2A.

In embodiments of the invention, a typical way of manufacturing the blade 10 is by first producing a flat blank that may already contain some of the overall geometric features of the eventual blade 10. Such a flat blank is illustrated in FIG. 4. The flat blank may be of uniform thickness. In a later manufacturing step, the flat blank may be bent or stamped or deformed so as to produce the final three-dimensional blade 10. Accordingly, one way of describing the plan view shape of the tip is by describing the shape of a flat blank that may be present in an intermediate step in the manufacturing process.

One possible geometry of the tip 20 is that, when the blade 10 is viewed from above (which may be referred to as plan view) in the flat sheet metal state, prior to being stamped or bent or deformed into the shape that created the trough geometry, the tip 20 may have a distal end that is a semicircle whose diameter is the width of the flat blank. In embodiments of the invention, the radius "T" of the tip 20, if the blade 10 is in a flat condition, before it is bent, formed, or machined into its eventual trough shape, may be between 0.05 and 0.5 inches.

In still further embodiments, the flat state of the blade 10 may have any of the shapes illustrated in FIGS. 5A-5F. For example, it is possible that, in plan view, the tip 20, could be semi-hexagonal or semi-octagonal as illustrated in FIG. 5C. In addition to the semi-hexagonal and semi-octagonal tip configurations, still other tip configurations are possible using polygons of any other desired number of sides. Such polygons could be portions of regular polygons (all sides and all angles being equal) as illustrated, or alternatively could be any other polygonal shape. The shape could alternatively be a continuously curved shape. There could alternatively be various other multi sided geometries that approximate the geometries shown.

Another possible way of describing the shape of the tip 20 of the blade 10 is its shape in plan view after the bending or forming into the three-dimensional shape of the blade. This is shown in FIGS. 6B, 6C.

FIG. 6B illustrates that the tip may be characterized by a minimum enveloping rectangle in plan (top) view. The tip 20 for purposes of this rectangle may be considered to begin when the profile departs from a constant-width body 30. This minimum enveloping rectangle of tip (top view) may have a tip width and a tip length. The ratio of these is an indicator of to what extent the tip is "swept back." The ratio tip length/tip width may be chosen to be between 0.1 and 2, more preferably between 0.3 and 1.2.

Figure 6C:
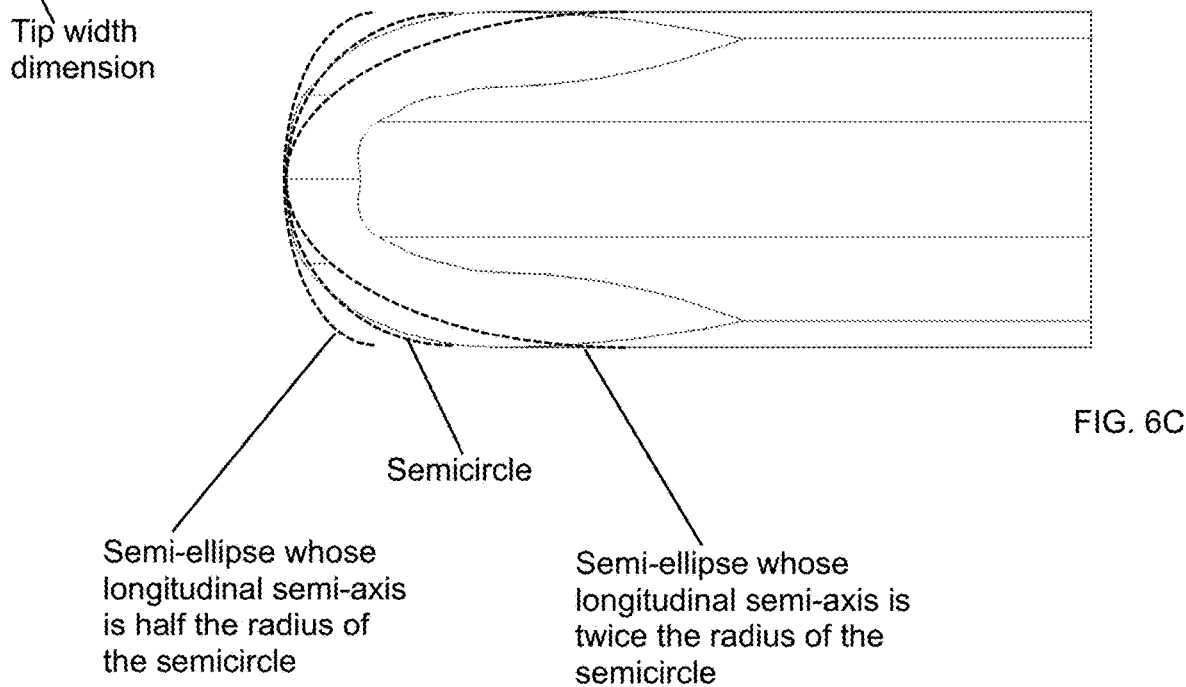

As a point of comparison, shown in FIG. 6C, it is possible to envision a hypothetical semicircle whose diameter equals the width of the blade (after the bending) in plan view, and which is tangent to the distal-most point of the tip 20 of the blade 10. (Such a semicircle might not exactly correspond to the semicircular end of the flat blank prior to bending, but it would be similar.) Similar to the just-described semicircle, it is possible to envision two hypothetical ellipses that also are tangent to the distal-most point of the tip 20 of the blade 10.

Each of these ellipses may be centered on the midplane of the blade 10. Each of these ellipses may have a lateral semi-axis that is equal to half of the width dimension of the body 30 of the blade 10. For one of these ellipses, the proximal-distal semi-axis may be one-quarter of the blade width dimension. For the other of these ellipses, the proximal-distal semi-axis may be the blade width dimension. In an embodiment of the invention, the distal edge of the blade 10, in plan view, may have a shape that lies between these two ellipses.

A common effect of these various configurations of the tip is that the three-dimensional shape of the tip becomes "swept back" such that the portion of the tip that actually contacts the subject material such as bone cement has a smaller width than the width of the body 30 in plan view, and has a smaller cross-sectional area than the body 30 has. As described elsewhere herein, it is believed that this contributes to concentrating the impact or compressive force into a smaller area for improved cutting, and also contributes to a sort of stability such that the tip 20 does not wander away from the working area. It is believed that there are optimum design parameters to achieve this, as described elsewhere herein.

Figure 6D:
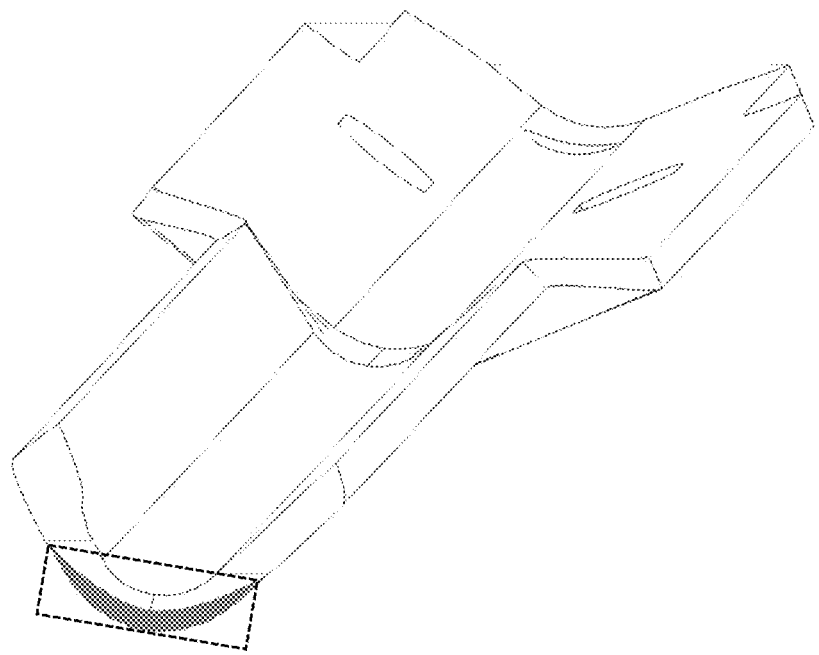
Figure 6E:
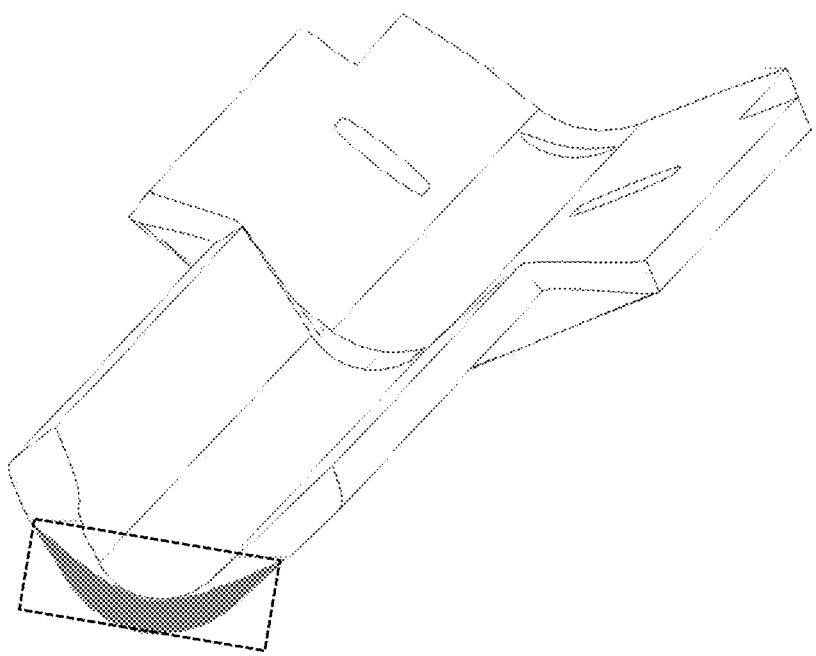
Figure 6F:
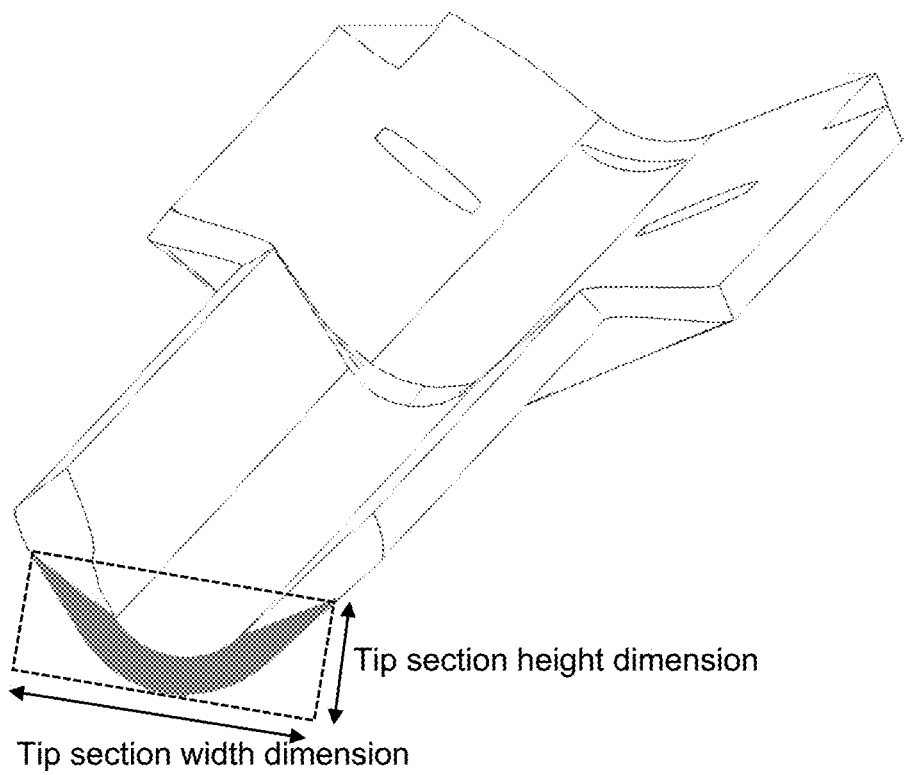
Figure 6G:
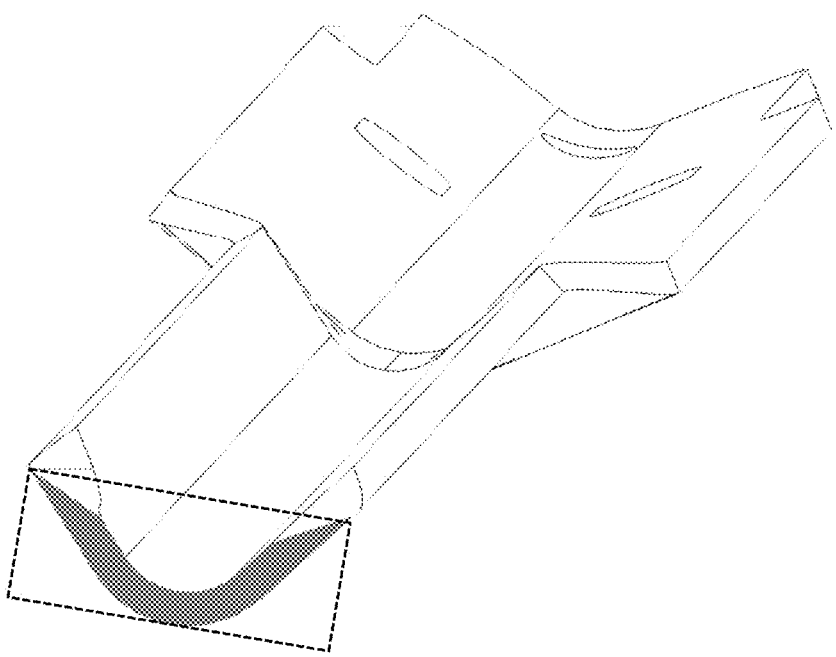
Figure 6H:
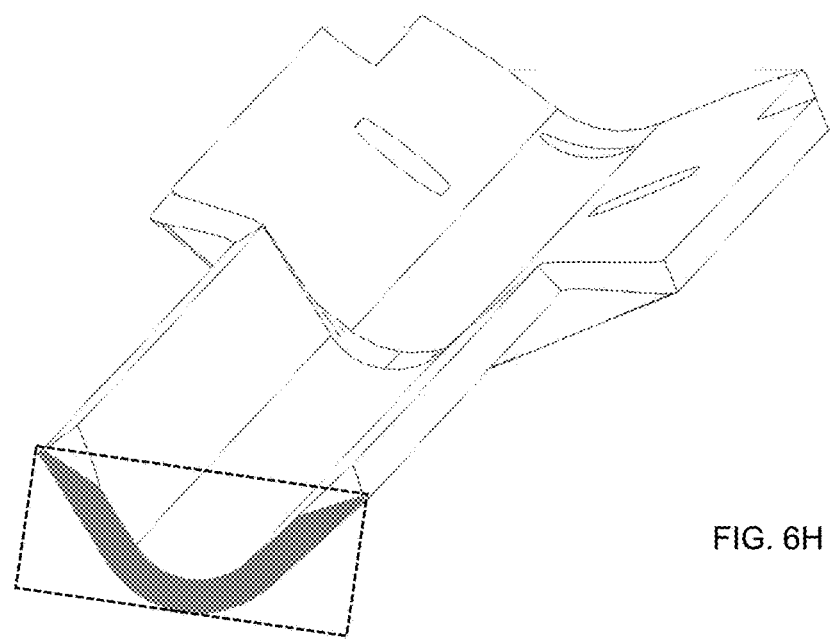

It is further possible to characterize the tip 20 as having a cross-sectional shape, which is shown in FIGS. 6D-6H for five different sectioning locations starting with the section in FIG. 6D being closest to the tip and sections in FIGS. 6E, 6F, 6G, 6H being progressively further away from the tip. At each of these sections there may be a trough radius of curvature and, if straight segments exist at that section, an included angle. At each section there may be a minimum enveloping rectangle, which may have a tip section width dimension and a tip section height dimension, as illustrated in FIGS. 6D-6H. At each section, a tip section aspect ratio may be defined as a ratio of the tip section width dimension to the tip section height dimension. The tip aspect ratio may range from 1.0 to 3.5. The tip aspect ratio may vary depending on where in the tip a particular section is taken. As can be seen, in some places the section may be crescent-shaped while in other places shape of the tip section may be more similar to the shape of the section through the body 30. The trough internal radius of curvature of the tip may be identical to that of the body, or it may be different. The tip internal radius of curvature may be between 2% and 40%, or between 5% and 25%, of the body width dimension. The tip internal radius of curvature may be between approximately 0.05 to 6.25, or between 0.2 to 4, times the tip thickness. The included angle of various sections of the tip, if such sections have straight-line segments that can define an included angle, may be identical to that of the body 30 or may be different. The tip aspect ratio may be identical to that of the body 30, or may be different.

Cutting Edge Details of the Tip

Embodiments of the invention may comprise a sharp distal edge suitable to cut bone cement or other material. The existence of a sharp distal edge may contrast, first of all, with the situation for certain ultrasonic tools which macroscopically have a similar distal end shape. The ultrasonic tools do not actually cut or chip bone cement, but rather they transmit vibrations to the bone cement, with the vibrations being tuned to the natural frequency of the bone cement through the blade, so as to generate heat and ultimately soften or melt the bone cement so that the tool can be pushed through the bone cement.

In embodiments of the invention, the tip 20 may have a cutting edge radius of no more than 0.010 inch. More generally, such cutting edge may be as sharp as is practically possible, and may be formed by grinding, for example.

In regard to location of the cutting edge with respect to the thickness of the blade 10, it is possible that the cutting edge can be either on the top surface of the blade, the bottom surface of the blade, or between the bottom and top surfaces of the blade. In general, the cutting edge may be adjacent to the concave surface of the tip 20 (referred to as the top side), or may be adjacent to the convex surface of the tip 20 (referred to as the bottom side), or may be in between. It is believed that, for good removal of bone cement, it is helpful if the cutting edge is directly at the convex (bottom) surface of the tip 20. This is referred to as top grind because if the sharp edge is formed by grinding, as is typically done, the removal of material by grinding would occur on the top (concave) surface of the blade 10. This is the configuration that is illustrated in FIGS. 6 and 7A. For this purpose the cutting edge may be located at the convex (bottom) surface of the tip 20 or within 10% of the body thickness thereof.

Referring now to FIG. 7A, there is shown a longitudinal cross section of the tip from FIG. 2A. In this figure, there is shown the bevel angle or edge angle "E" to which is the angle the cutting edge is beveled. FIG. 7B also shows these angles in profile-including "top", "bottom" and "both" top and bottom (center) cutting angles. This angle "E" may be chosen to be between 5 and 60 degrees for "top" and "bottom" cutting edges. It is illustrated as 25 degrees. In the case of a blade 10 that is beveled on both top (concave) and bottom (convex) surfaces, the included angle "E" between the beveled edges may be chosen to be between 10 and 120 degrees.

For this illustrated configuration, in an embodiment of the invention, the bottom-most portion of the tip 20 may lie on the same plane that runs along the body 30 of the blade 10. During use for removal of bone cement, this feature allows the blade 10 to slide or contact right up against the bone (such as the internal surface of the intramedullary canal) and parallel to the bone while the blade 10 is cutting into the bone cement. If the cutting edge were at the top (concave) surface of the blade could not run right up against the bone and still be parallel to the bone, and its cut would have to be at least the blade thickness away from the bone. If the cutting edge were located in the middle of the thickness of the blade material, or somewhere between the top and bottom surfaces, this also would create the situation where the cutting edge would be some distance away from the bone when the blade is parallel to the bone. This ability for the blade to run parallel to the bone while running right up against the bone is believed to be important when the blade 10 is removing bone cement in the intramedullary canal, which is a common area of bone cement use. In the intramedullary canals there is limited room to angle the blade 10 to achieve a cut against the bone. So, in order to remove all the bone cement, which is a desired outcome, it is helpful for the external (convex) surface of the blade 10 to slide or contact right up against the bone (such as the internal surface of the intramedullary canal) to remove all the bone cement, i.e., for the cutting edge to coincide with the bottom (convex) surface of the tip of the blade.

An embodiment of the invention has the cutting edge shaped into the tip 20 from the top side as shown in FIGS. 7A-8C. This may be formed by grinding. The grinding or machining of the cutting-edge angle "E" may entail following the curve or geometry of the blade tip around its edges until they become tangent or coincident with the sides of the blade body. This grinding of the edge may also include a tapering off of the blade edge as it transitions from the tip to the body.

The tapering of the edge of the blade is illustrated in FIGS. 7A-8C. In embodiments of the invention, it is further possible that the blade edge angle "E" may also vary as a function of position along the tip edge to achieve a more desirable cutting action. For example, it may be desirable to have a larger Edge Angle "E" at the base of the trough and a smaller Edge Angle "E" as you move away from the trough up the sides of the tip. FIGS. 8B and 8C show a view of one leg of the "rounded-V" of the tip.

The blade 10, or at least its tip, may have a hardness that is suitable to cut the material of interest such as bone cement. For example, the hardness may be HRC 35 (Hardness Rockwell C of 35) or harder. The blade 10 may be made of or may comprise stainless steel, for example, or other suitable metal.

Transition Region and Hub

Proceeding further proximally along the proximal-distal direction of blade 10, there may be a transition region 40 that is continuous with body 30. Still further proximally, there may be a hub 50 that is continuous with transition region 40. The hub 50 may be suitable to be grasped by a tool such as a pneumatically or electrically operated power tool, or may be suitable to be struck with a hammer. There may be geometric differences between the hub 50 and the body 30, which may make it appropriate to provide a transition region 40.

In an embodiment, the hub 50 may be such that, in a cross-section of the hub 50 taken perpendicular to the proximal-distal direction, the hub 50 has a hub cross-section, and the hub cross-section can be enveloped by a minimum hub enveloping rectangle that is a smallest rectangle that can enclose the hub cross-section. Similar to the previously defined minimum enclosing rectangle for the body, the minimum hub enveloping rectangle is tangent to the concave surface of the hub at the underside of the hub, and elsewhere the rectangle touches various corners of the edges of the hub cross-section. This minimum hub enveloping rectangle may have a hub width dimension and a hub height dimension, and a hub aspect ratio can be calculated as a ratio of the hub width dimension to the hub height dimension. In embodiments, the hub aspect ratio may range from 0.1 to 10.

In embodiments, the hub aspect ratio could be different from the body aspect ratio, which is what is illustrated in FIG. 9. Alternatively, if desired, the hub aspect ratio and the body aspect ratio could be equal to each other. The hub bend radius or minimum radius of curvature could be the same as the body bend radius or minimum radius of curvature. Alternatively, these quantities could be different from each other if desired.

In embodiments, the hub 50 width dimension may be greater than the body width dimension. For example, this may provide increased structural strength of the blade 10 near where the blade is gripped by a power tool. Such space for strength and gripping features might be unavailable for the portion of the body 30 of the blade 10 that is intended to fit within the intramedullary canal.

In embodiments, the hub 50 may comprise holes or other geometric features for interfacing with a driver tool or other components. In FIG. 9, hole 60A may be suitable for interfacing with a driver tool. Holes 60B and 60C may be suitable for interfacing with a splash guard. Such a splash guard is illustrated in FIG. 11.

It can be understood that, if desired, still other interface configurations may be designed for the hub 50, as may be desired for a particular driving tool that may hold blade 10.

In embodiments, the blade 10 may have dimensions appropriate for fitting inside typical dimensions of an intramedullary canal that contains bone cement needing to be removed during revision surgery. For example, the width dimension of the body 30 may be in the range of 0.2 inch to 1.0 inch. The length of the body 30 may be in the range of 1.0 inch to 18 inch.

The blade 10 may comprise metal such as stainless steel and may have a thickness suitable so that the blade can withstand a compressive or impact force along the proximal-distal direction of at least 10 N without buckling, or at least 50 N.

Embodiments of the invention are further described, but are in no way limited, by the following Examples. A series of tests was performed to optimize the design of the blade, by experimenting with actual cutting of materials including bone cement.

Example 1

Initially, a first round of blade testing was a configuration survey, in which we tested various widely varying geometries (see FIG. 12) to see what overall geometric category performed best. We tested flat blades with flat cutting edges (like a conventional chisel), round edges, and pointed triangular cutting edges. We tested various widths of these blades, including 4 mm and 6 mm widths of several blade designs. (This is smaller than the width of the blade 10 described elsewhere herein.) We tested concave blades having rounded and flat cutting edges. We tested "rounded-V" shaped blades with flat and sloped edges. All blades tested had top ground edges.

From this testing, we found that the sloped (swept back) "rounded-V" shaped blades cut significantly better than the various other blades (see Table 1). We determined that the pressure concentration at the point of the swept-back "rounded-V" allowed the blade to penetrate and remove the tough bone cement especially well. The "rounded-V" shape allowed the cutting to continue as a slicing action through the bone cement. The shape of the swept-back "rounded-V" provided structural support for the cutting edge while keeping the cutting edge rigid during the cutting process. It is believed, although it is not wished to be limited to this explanation, that a greater "swept back" blade design that produces a more pronounced pressure concentration at the point of the blade tip 20 will impart more local pressure to the surface of the bone or bone cement because the blade force is concentrated onto a smaller surface area. A blade design having small or no "sweep back" (such as, in the extreme, a conventional chisel) will impart less local pressure because the blade force is spread out over a larger surface area of the material it is cutting. These findings are summarized in Table 1.

TABLE 1

| Blade | Results | Score |
| --- | --- | --- |
| Flat Edge - 4 mm wide | Dug down into cement without creating chips | 3 |
| Flat Edge - 6 mm wide | Difficulty in getting it to dig into cement | 2 |
| Round Edge - 6 mm | Started fair and became bogged down quickly | 3 |
| Triangular - 6 mm | Started good and became bogged down quickly | 4 |
| Concave - 4 mm | Slow cutting with minimal chipping | 4 |

TABLE 1-continued

| Blade | Results | Score |
|---|---|---|
| Concave - 6 mm | Very slow cutting with no chipping | 3 |
| V bend - Straight 4 mm | Started good, became slower, minimal chipping | 4 |
| V bend - Straight 6 mm | Started good, became slower, moderate chipping | 3 |
| V bend - Slanted 4 mm | Good cutting, much faster than others, good chipping | 7 |
| V bend - Slanted 6 mm | Good cutting, a little slower than 4 mm V bend slanted, good chipping | 6 |

As a result of this configuration survey, we selected and focused on concave trough-shaped blades that had some slanted sweep-back, and we sought to further optimize that category of blade geometry. For this optimization study, we designed a number of variations of this design in order to find an optimum cement removal blade (see Table 2 and FIG. 13). For this optimization study, the blades were made by cutting or forming a Flat Blank from sheet metal, and then the Flat Blank was bent or stamped to make it into a three-dimensional rounded-V trough shape. For all of the experiments in this optimization study, we used the same Flat Blank and we only varied the details (included angle, bend radius) of the rounded-V shape into which the Flat blank was bent or stamped. For the blades tested in this group of experiments, the Flat Blank configuration of the blades, prior to bending, was such that the tip at the distal end was shaped as a semicircle having a diameter equal to the blade width in the Flat Blank condition. All of the experimental blades in this group of tests had the same width of the Flat Blank of the blade. The parameters that we varied were the included angle (A) and the Bend Radius (R). The included angle was varied as follows: 80, 100, and 120 degrees. The Bend Radius was varied as follows: 0.03 inch, 0.09 inch. We decided on combinations of these variables that we thought would give us the best opportunity of success. Due to resources, we built and tested only the blades having 0.09 inch Bend Radius (the middle value of bend radius) in the three different "V" angles, and also one other case in which the bend radius was 0.03 inch.

All of these blades were ground to a cutting edge that had a 25 degree taper angle at the outer (convex) surface of the blade. All of the blades were tested with the same instrument on the same type of bone cement block (see FIG. 8 for test setup). All blades were tested at 3600 strokes per minute using a Palix Medical LLC VersaDriver™ Pneumatic Osteotome. Results for each blade were judged subjectively by the design engineer who was performing the test, and an overall score was determined by that engineer. The tests were performed twice, and Test 1 and Test 2 were performed by different engineers in order to obtain two different independent opinions about the subjective test results. Results were evaluated by a score and a description of the cutting result. The score was a relative rating of the tested blade's cutting ability compared to a hypothetical ideal blade that would cut with ideal control and speed. The purpose for having two different engineers evaluate the blades was to get two different independent opinions.

The last entry in the table, CRB-X, somewhat resembled the CRB-02 design but it had a slightly sharper included angle "A" at 60 degrees, and its bend radius of 0.03 inch also was sharper than that of CRB-02. It was found that this blade provided the fastest cutting speed of all the blades, but that blade was very difficult to control and repeatedly wandered away from the desired path.

TABLE 2

Summary of tests of rounded-V shaped blades

| Blade | Trough angle | Bend radius | Results | Score |
|---|---|---|---|---|
| Test 1 (by Engineer 1) | | | | |
| CRB-02 | 80 | 0.09 | Cut really well. Takes out lots of small chips quickly. Great control | 10/10 |
| CRB-04 | 100 | 0.09 | OK. Digs in a little and wants to take out larger chips. Less control than CRB-02 | 7/10 |
| CRB-06 | 120 | 0.09 | Really digs into the bone block. Slow cutting and chips are large. Least control | 4/10 |
| Test 2 (by Engineer 2) | | | | |
| CRB-02 | 80 | 0.09 | Very controlled. Fast cutting | 10/10 |
| CRB-04 | 100 | 0.09 | Slower than CRB-02, digs in more before separation of chips. Chips larger than CRB-02. | 8/10 |
| CRB-06 | 120 | 0.09 | Slower to create chips. Chips bigger than CRB-02 and CrB-04. Bogs down during cutting. | 5/10 |
| CRB-X | 60 | 0.03 | Fastest cutting speed of all the blades, but very difficult to control; wanders | |

It can be seen in Table 2 that Blade design CRB-02 was preferable. All of results from both phases of the testing (both the configuration survey and the optimization study) are summarized in FIG. 13.

FIG. 14 is a photograph showing the CRB-02 prototype blade cutting bone cement during testing. For this testing, the axial force on the blade was provided by Palix Medical LLC's Versa Driver Pneumatic Osteotome. This is the blade that was judged to give the best performance of all of the blades that were tested. It can be seen that the blade chips away at the bone cement resulting in the creation of small chips, which is what is considered desirable for the intended application.

Example 2

Several orthopedic surgeons have used the described blade both in a laboratory setting and in surgery. All of them had commented, prior to trying the described blade, that they were reluctant to use a powered instrument to remove bone cement in the intramedullary canal of the femur, because if the tool were to wander from its intended location there would be a chance of the tool perforating the femur and causing significant damage.

One orthopedic surgeon, who had not yet used the blade of an embodiment of the invention, planned a very difficult revision surgery in which he had to remove a hip implant having an unusually long femoral stem that was implanted into the femur. He planned that several of his instrument suppliers would bring a wide variety of equipment into the surgery. After trying all of the available instruments during the surgery without success, he tried a blade of an embodiment of the invention. He started using the blade in a very conservative manner, but soon was using it under full power and was very confident in its use. In 5 minutes of surgical time using a blade of an embodiment of the invention, he completed the work, and he estimated that it would have taken him another two hours of surgical time to do the same work manually. He plans to use the blade frequently, because of the controllability that it provides, along with its cutting efficiency.

An embodiment of the invention can be a method of cutting bone cement, comprising providing a blade of an embodiment of the invention, and causing the blade to repeatedly strike the target bone cement suitably to cut or remove the bone cement.

Scoring Blade

In an embodiment of the invention, there may be provided a blade 2010 as illustrated in FIGS. 17A-17G. Such a blade may be referred to as a scoring blade and may be suitable to create axial cuts such as slots or grooves in bone cement that may be present on internal surfaces of a wall of an intramedullary canal.

Referring now to FIG. 17A, blade 2010 may comprise in sequence, a guidance region 2015, a cutting region 2030, a transition region 2040, and a hub 2050. These components are listed proceeding in sequence from distal (guidance region 2015, being closest to the patient) to proximal (the hub 2050, being closest to the user). The blade 2010 may have a longitudinal direction 2012 that is a proximal-distal direction. In an embodiment, guidance tip 2015 and cutting region 2030 may be part of a flat planar portion of the blade 2010.

The blade 2010 may, as illustrated in FIG. 17A, have a blade thickness T, which may be substantially constant throughout the blade 2010. Such construction may be consistent with manufacturing the blade 2010 starting from constant-thickness sheet material and later forming the blade into a three-dimensional shape such as by stamping or bending. The blade thickness T of blade 2010 may be 0.042 inch, or more generally in the range of 0.010 inch to 0.125 inch. Alternatively, the blade thickness could be tapered or of varying thickness.

Hub 2050 may have a geometry that is non-planar. Hub 2050 may have a cross-sectional shape, in a cross-section taken in a sectioning plane that is perpendicular to longitudinal axis 2012. As illustrated, hub 2050 has a cross-sectional shape that is generally V-shaped, but with the vertex of the V being less than fully sharp. In FIG. 17A, the vertex is shown as being a rounded vertex. Of course, the vertex could if desired be sharp. Hub 2050 may have a concave surface and a convex surface opposed to the concave surface.

Hub 2050 may be suitable to be received in a chuck that is capable of gripping the hub 2050 of blade 2010. The gripping action of a chuck onto blade 2010 may be provided by any one or more of various elements that can urge or bear against respective surfaces of the hub 2050, or may simply constrain the location of hub 2050 within a desired close range. The chuck could be part of a larger tool, which could be any of a pneumatically powered tool, an electrically powered tool, or a hand-held tool, or generally any kind of tool or instrument. Such a chuck and tool are illustrated in commonly assigned U.S. Pat. No. 10,595,879 and in commonly-assigned U.S. patent application Ser. No. 17/402,511. It is still further possible that chuck 2050 or an equivalent may be suitable to be struck on its proximal end with a hammer, mallet or similar instrument, such as by having a flat surface that is generally perpendicular to a longitudinal axis of the blade 2010. It is still further possible that hub 2050 may be suitable to be struck on its proximal end with a hammer, mallet or similar instrument, such as by having a flat surface that is generally perpendicular to a longitudinal axis of the blade 2010. In such a situation, there might be no need to actually grip hub 2050 in a chuck.

Between hub 2050 and cutting region 2030 there may be a transition portion 2040. A transition portion 2040 is further illustrated in commonly assigned U.S. Pat. No. 10,595,879 and in commonly assigned U.S. patent application Ser. No. 17/402,511. In the transition portion 2040 that is nearest cutting region 2030, the transition portion 2040 may be nearly flat. In the transition portion 2040 that is nearest hub 2050, the transition portion 2040 may have almost the same cross-section as hub 2050. In between, there can be transition surfaces that are smoothly curving surfaces appropriate to achieving the desired geometric transition. It is believed that the use of transition region 2040 creates a situation where there is less of a stress concentration factor than in a situation of abrupt geometric change.

In embodiments, the overall width of the cutting region 2030 of blade 2010 may be 0.2 inches to 1.0 inches.

In an embodiment, the Scoring Blade 2010 may comprise a flat blade portion that has a notch cut into its side or end, creating a small cutting edge 2032 of a defined depth and also creating a guidance region 2015 that extends beyond the cutting region 2030.

In regard to the guidance region 2015 and referring now to FIGS. 17A-17G, a portion of the guidance region 2015 may have a guidance edge 2016 that is generally parallel to the longitudinal direction 2012 of blade 2010 or to the direction of motion of blade 2010 during a cutting procedure. During use, such guidance edge 2016 or guidance surface may ride on undisturbed bone cement that is deeper in the intramedullary canal than already-scored bone cement associated with the score that is in progress.

In an embodiment, the guidance region 2015 or guidance edge 2016 may have at least some portion or surface that is not sharp and is not adapted for cutting. This may be a longitudinal surface that is generally parallel to the longitudinal direction 2012 of blade 2010. For example, it may be considered that all or at least a majority of the edges or surfaces of guidance region 2015 may be less sharp than the cutting edge 2032 of the cutting region. It may be considered that all or at least a majority of the edges or surfaces of guidance region 2015 that are generally parallel to the longitudinal direction 2012 of blade 2010 may be less sharp than the cutting edge 2032 of the cutting region. It may be considered that all or at least a majority of the edges or surfaces of guidance region 2015 may have an edge radius of curvature greater than 0.002 inch. It may be considered that in general, for cutting, a cutting edge radius of curvature of 0,010 inch or greater is not suitable for cutting. A cutting edge radius of curvature between 0,010 inch and 0.002 inch is possibly suitable for cutting but not preferred for cutting. A cutting edge radius of curvature of less than 0.002 inch is preferable for cutting. In an embodiment, the distal-most edge or surface of the guidance region 2015 may be not sharp or not adapted for cutting.

Guidance region 2015 may control the positioning of the cutting edge 2032 for penetrating or cutting bone cement. As a result, the guidance region 2015 may bear against intact bone cement deeper into the intramedullary canal, while the cutting edge 2032 associated with the notch cuts a generally axially-oriented groove into the bone cement. This gives the surgeon great control over how deep a cut is made into the bone cement so as not to go so deep as to cut into the bone. The tip of the guidance region 2015 can be flat, chamfered, or rounded so it does not catch or dig into the bone or bone cement as it slides along the bone surface of the bone or bone cement.

Although the guidance edge 2016 is illustrated as being straight and generally parallel to the longitudinal direction 2012 of the blade 2010, the guidance edge 2016 also could have other shape if desired.

Referring now to FIGS. 17B and 17C, it is illustrated that the cutting edge 2032 of the scoring blade 2010 may be generally straight and may have a defined angle with respect to the long axis of the blade 2010. This angle is labeled as e in FIG. 17C. In FIG. 17D, the angle θ is illustrated as being less than 90 degrees, which may be referred to as a forward-sloping cutting edge 2032. During use, such an angle on the cutting edge 2032 can be expected to provide a force component acting on the blade 2010 which would tend to urge the guidance edge 2016 up against the not-yet-disturbed bone cement surface that is located deeper in the intramedullary canal. This is believed to be a desirable feature as it will help to keep the depth of cut consistent. In FIGS. 17E-17F, it is shown that the cutting edge 2032 is perpendicular to the longitudinal direction of blade 2010, in which case θ is 90 degrees. It is also possible that the cutting edge 2032 could be sloped such that θ is greater than 90 degrees, if desired. The cutting edge 2032 could also be shaped in various geometric shapes, such as curved, and it could be sharp-edged or could be serrated, etc.

Referring now to FIG. 17E, in an embodiment, notches may be cut into both sides of the cutting region 2030 of blade 2010. The notch may define the cutting edge 2032, which has a width W. The depths, or widths, of the notches could be equal on opposite sides of the cutting region 2030, as illustrated in FIG. 17B and FIG. 17E. Alternatively, as illustrated in FIG. 17F, the width of the notch could be different on the two different sides of the blade, illustrated as W1 on one side of the blade 2010 and W2 on the other side of the blade 2010. The providing of two different cutting edge widths W1, W2 on opposite sides of the blade 2010 allows for cutting more or less deeply into the bone cement, depending on which edge of the blade 2010 is used for cutting, without removing a blade 2010 from the power tool and replacing it with a differently dimensioned blade 2010. This can be useful when bone cement has different local thicknesses in different places in a particular patient. It is illustrated in some illustrations that the notch width or inset distance on one side of the blade 2010 is identical to the notch width or inset distance on the other side of the blade. It also is illustrated in FIG. 17F that these two distances could be different from each other. In such a situation, the surgeon would have two options regarding how to use the blade 2010. Two different depths of cut would be available to the surgeon, without a need to remove and replace the blade 2010 from a power tool. In order to change the depth of cut, the surgeon could simply withdraw the blade from the intramedullary canal, re-orient the power tool including the blade 2010, and then re-insert the blade 2010 into the intramedullary canal and perform scoring cuts using the other edge of the blade 2010. This could be done for different scoring cuts, or for different portions of a single scoring cut. This is illustrated in FIGS. 17E-17F for a cutting edge 2032 that is generally perpendicular to the long axis 2012 of blade 2010.

In embodiments, the cutting edge 2032 could be Center Ground, Top Ground, or Bottom Ground, or some other geometric configuration, similar to what was illustrated in FIGS. 7A-7C. A center ground cutting edge 2032 is what is illustrated in FIGS. 17A-17G. This edge may be ground, and may have a local radius of curvature that is <0.010 inch, or <0.002 inch, or generally may be as sharp as possible, In an embodiment, it also is possible, referring now to FIG. 17G, that some portion of the distal end or tip of the guidance region 2015 could be sharpened and could be suitable for cutting. Such sharpening could allow a surgeon to perform at least some cutting using the distal tip of scoring blade 2010, without removing blades 2010 from the power tool and replacing them. The tip may be ground to a sharp edge similarly to what is illustrated in FIGS. 7A-7C. The local shape of the sharpened region could be any desired shape. The distal edge of the sharpened region is illustrated in FIG. 17G as having a short straight segment, but more generally any shape is possible. This edge may be ground, and may have a local radius of curvature that is <0.010 inch, or <0.002 inch, or generally may be as sharp as possible, In the blade of FIG. 17G, it can be seen that, proceeding around the perimeter, there is a cutting edge 2032, followed by a non-cutting edge which is guidance edge 2016, followed by a sharp feature or edge at the tip of guidance region 2015, followed by a non-cutting edge which is guidance edge 2016, followed by a cutting edge 2032.

In embodiments, the blade 2010 may have dimensions appropriate for fitting inside typical dimensions of an intramedullary canal that contains bone cement needing to be removed during revision surgery. For example, the width dimension of the body 2030 may be in the range of 0.2 inch to 1.0 inch. The length of the body 2030 may be in the range of 1.0 inch to 18 inch. The blade 2010 may comprise metal such as stainless steel and may have a thickness suitable so that the blade 2010 can withstand a compressive or impact force along the proximal-distal direction of at least 10 N without buckling, or at least 50 N.

Surgical Method

An embodiment of the invention can also comprise a method of removing bone cement from the wall of an intramedullary canal at a revision site, using the various blades described herein. The method may comprise two steps, with the first step being scoring the bone cement using an axial scoring blade 2010, and the second step being removing bone cement using a blade such as the Cement Removal Blade 10.

Axial scoring blade 2010 may be used in the first step. By making these axial cuts through at least some of the depth of the bone cement, the strength of the bone cement layer is reduced significantly, and the bone cement may be sectioned into axial strips that can then be very quickly chipped away with the CRB 10, creating large chips of bone cement and also exposing a bone surface that is clean and well preserved. These are two very desirable outcomes. Currently, removing bone cement during a revision surgery is a time-consuming and difficult step. Leaving a clean bone surface without gouges and chips, one where the bone is well preserved, will maintain the structure and strength of the bone and provide a favorable surface for attachment of a new implant. Furthermore, reducing the duration of surgery is always beneficial for the patient.

In an embodiment, the Scoring Blade 2010 may be used with the VersaDriver™ pneumatic osteotome as disclosed in U.S. patent application Ser. No. 17/402,511 and U.S. patent application Ser. No. 63/066,089. Alternatively, the described scoring blade 2010 could be driven by any automated or manual type osteotome system, or it could be used by itself as a manual osteotome driven by a hammer or mallet.

The scoring step may then be followed by using a CRB blade 10 as disclosed herein, or by cutting using any other type of blade. It is believed that the process of removing bone cement from bone may be significantly improved by use of the Scoring Blade 2010 in a process as described herein.

Reference is now made to FIGS. 18A-18C. In FIGS. 18A-18C, for simplicity of illustration, the bone cement is shown as being an annulus of uniform thickness, and the bone is also shown as being an annulus. FIG. 18A shows the scoring blade 2010 in position with respect to a cut end of an intramedullary canal at the beginning of a scoring cut. This is shown with other scoring cuts having already been made at other angular locations around the same intramedullary canal.

FIG. 18B shows the same blade 2010 making the same scoring cut, but with the blade 2010 located deeper in the intramedullary canal with a portion of the scoring cut completed. FIG. 18C is a cutaway version of FIG. 18B.

In an embodiment of the method, the scoring blade 2010 may be used to create one or more axial scoring cuts along the surface of the bone cement that covers the bone. Typically, this scoring cut may be performed on the bone cement surface that lines the intramedullary canal after an implant has been removed during revision surgery. As the cutting procedure progresses, the scoring blade 2010 may advance and the region of undisturbed bone cement may recede.

Typically, the bone cement present at the start of a revision surgery may be of varying thickness, varying as a function of either or both the position along the long direction of the intramedullary canal and the angular position around the perimeter of the intramedullary canal.

During use, the guidance edge 2016 of the blade 2010 may be positioned so as to bear against the bone cement that is more distal with respect to the area that is to be cut by the cutting edge of the blade 2010. The not-yet cut bone cement may provide a natural depth guide for the blade 2010 so that the blade 2010 does not cut deeper than the Notch Width. The scoring cut may have a cut width and a cut depth. In embodiments, the cut width of the scoring cut may be approximately equal to (or slightly greater than) the thickness of the scoring blade 2010. The depth of the scoring cut in the bone cement or other material depth may be approximately equal to the notch dimension or inset distance (W, W1, W2 in FIGS. 17E-17F) of the blade 2010, due to the functioning of the guidance edge 2016 as a follower along the surface of the undisturbed bone cement or other material.

In regard to the depth of the scoring cut and the dimensions of the Scoring Blade 2010, Scoring Blades 2010 of various notch widths can be provided to accommodate different local thicknesses of bone cement. Scoring blades 2010 can be swapped out of the powered tool in order to change the depth of the scoring cut. Also in this regard, a non-symmetric scoring blade 2010 as described herein can be used, such that the depth of scoring cut can be varied by cutting with one side or cutting edge of the blade 2010 rather than the other side or cutting edge of the blade 2010, simply by changing the orientation of the power tool.

Of course, it is possible to use the scoring blade 2010 to cut through substantially the entire or exact thickness of the bone cement on the internal surface of the intramedullary canal. However, typical surgical conditions are such that the thickness of bone cement might vary from one location to another, the bone cement might not be fully visible to the surgeon, it might not be possible to exactly ascertain the bone cement thickness or match the cut depth to the local thickness of bone cement, and it is desirable to perform surgery with reasonable speed. In view of considerations such as these, it is believed that, even if it is not possible to exactly match the cutting depth to the local bone cement thickness, it is helpful if axial scoring is performed such that the cutting depth is at least approximately 50% of the local bone cement thickness. It is believed that scoring to this extent will sufficiently weaken the strength of the bone cement cylinder lining the bone canal so that a follow-on blade such as the Cement Removal Blade 10 can do its work more efficiently than would occur in the absence of axial scoring of the bone cement. In FIG. 18A-19B, it is illustrated that the scoring blade 2010 cuts through some of the thickness, but not the entire thickness, of the bone cement, thereby avoiding the possibility of cutting into the bone itself. It is believed that it is preferable to cut a scoring cut through a portion of the bone cement while leaving a little bit of the bone cement unscored, rather than cutting so deeply as to score some of the bone itself. Typically, the scoring operation would only be a preparatory step, anyway, in preparation for a more complete cement removal using a different blade such as blade 10 described elsewhere herein.

In regard to the spacing between adjacent axial scoring cuts, it is believed that, up to a reasonable number of axial scoring cuts, the more axial scoring cuts are created in the bone cement, the easier and more readily the bone cement is able to be removed. It is believed to be desirable for the distance between the axial scoring cuts to be roughly equal to the width of the tip or body of the CRB blade 10, or not more than two times the width of the tip or body of the CRB blade 10.

In still other embodiments, the axial scoring cuts can be achieved by other means such as small saws, files, osteotomes, sagittal saws, fine toothed rasps, or other cutting instruments capable of creating axial cuts through bone cement. Such cuts can be made either under powered motion from a power tool or by the use of tools by hand or with hand driving means such as hammers or mallets.

FIGS. 18A-18C show a CRB 10 cutting bone cement that remains between the scoring cuts. FIG. 18A shows the axial scoring blade 2010 in position at the end of the intramedullary canal, at the beginning of the process of making a scoring cut. It can be noted that in FIG. 18A, other scoring cuts have already been made at other angular positions around the intramedullary canal. FIG. 18B shows the same blade but deeper in the intramedullary canal partway through the process of making that scoring cut. FIG. 18C is a sectioned view of FIG. 18B.

After the axial scoring cuts are made with the Scoring Blade 2010, a blade such as the blade 10 described elsewhere herein may be used to chip away at the bone cement that remains between the axial scoring cuts, as well as chip away at any bone cement that may remain at the axial scoring cuts if the axial scoring cuts do not penetrate through the bone cement all the way to the bone. It is believed that after the first amount of bone cement in between one or more axial scoring cuts is removed, the process of breaking up or cutting or removing the remaining bone cement should become significantly easier. This is shown in FIGS. 20A-20B. FIG. 19A shows Cement Removal Blade 10 in the process of cutting a region of bone cement that is located between two adjacent score cuts. As illustrated, the width of the body 30 or tip 20 of blade 10 is approximately equal to the distance between adjacent score cuts. FIG. 19B is a sectional view of FIG. 19A.

EMBODIMENTS

Embodiments of the invention are further described but are in no way limited by the following embodiments:

Embodiment 1. A blade for use in cutting, said blade comprising:
a guidance portion;
a cutting portion that is continuous with said guidance portion;
a transition portion that is continuous with said cutting portion; and
a gripping portion that is continuous with said transition portion,
wherein said blade has a longitudinal axis,
wherein said cutting portion is planar having a cutting portion planar surface facing in an upward direction and has at least one cutting edge that is adapted for cutting,
wherein said gripping portion has an upward-facing surface facing generally in said upward direction and said upward-facing surface does not entirely lie in a single plane, and
wherein said transition portion has a three-dimensional surface transitioning between said cutting portion and said gripping portion,
wherein said guidance portion comprises edges that are less sharp than said cutting edge of said cutting portion.

Embodiment 2. The blade of embodiment 1, wherein said guidance portion edges have a local radius of curvature that is larger than 0.002 inch.

Embodiment 3. The blade of embodiment 1, wherein one of said guidance portion edges is generally straight and parallel to said longitudinal axis, said straight edge being less sharp than said cutting edge of said cutting portion of said blade.

Embodiment 4. The blade of embodiment 1, wherein said guidance portion has a distal-most end that, when viewed from said upward direction, is convex having a radius of curvature of at least one-tenth of a side-to-side dimension of said guidance portion.

Embodiment 5. The blade of embodiment 1, wherein said guidance portion has a distal-most end having radius of curvature greater than 0.002 inch.

Embodiment 6. The blade of embodiment 1, wherein said guidance portion has a distal-most end that is ground to a cutting edge having a radius of curvature less than 0.010 inch.

Embodiment 7. The blade of embodiment 1, wherein said guidance portion has a side-to-side dimension smaller than a side-to-side dimension of said cutting portion.

Embodiment 8. The blade of embodiment 1, wherein, where said guidance portion meets said cutting portion, an inset distance on one side of said blade is different from an inset distance on an opposed side of said blade.

Embodiment 9. The blade of embodiment 1, wherein said cutting portion comprises a cutting surface and said cutting surface is top-ground, bottom-ground, center-ground, or ground to a sharp edge that is located between opposed surfaces of said cutting portion.

Embodiment 10. The blade of embodiment 1, wherein said cutting surface angle is forward-facing, forming an acute angle of less than 90 degrees with respect to a longitudinal axis of said guidance portion.

Embodiment 11. The blade of embodiment 1, wherein said cutting surface angle is perpendicular to said longitudinal direction, or is rearward-facing.

Embodiment 12. The blade of embodiment 1, wherein said gripping portion is suitable to be gripped in a power tool.

Embodiment 13. The blade of embodiment 1, wherein said gripping portion is suitable to be struck by a hammer.

Embodiment 14. A method of removing bone cement from an internal surface of an intramedullary canal, said method comprising:
cutting an axial score cut in said bone cement, said axial score cut having a cut width and a cut depth, while leaving an undisturbed region of said bone cement adjacent to said score cut; and
cutting said undisturbed region of said bone cement adjacent to said score cut.

Embodiment 15. The method of embodiment 14, wherein said cutting said axial score cut and said cutting said undisturbed region are performed using different cutting blades.

Embodiment 16. The method of embodiment 14, wherein said cutting said axial score cut is performed using a blade that comprises a guidance portion, a cutting portion that is continuous with said guidance portion; a transition portion that is continuous with said cutting portion, and a gripping portion that is continuous with said transition portion.

Embodiment 17. The method of embodiment 14, wherein said cutting said axial score comprises cutting to a depth of at least half of a local thickness of said bone cement.

Embodiment 18. The method of embodiment 14, wherein said cutting said axial score comprises cutting to a depth less than a local thickness of said bone cement.

Embodiment 19. The method of embodiment 14, further comprising cutting an undisturbed region of said bone cement that is located deeper within said bone cement than a bottom of said score cut.

Embodiment 20: The method of embodiment 14, wherein said method comprises cutting a plurality of said score cuts, wherein adjacent ones of said score cuts are separated from each other by a distance that is between one and two times a width of a tip or body of a blade used to cut said undisturbed region of said bone cement.

Embodiment 21. The method of embodiment 14, wherein said cutting said undisturbed region is performed using a blade that comprises:
a tip, said tip having a tip thickness measured perpendicular to a local surface of said blade; and
a body, proceeding proximally from said tip, said body having a body width dimension;
wherein said body and said tip both extend generally along a proximal-distal direction,
wherein said tip is trough-shaped having a tip concave surface and an opposed tip convex surface,
wherein said tip has a tip cross-section, taken perpendicular to said proximal-distal direction,
wherein, said tip cross-section has a concave surface that has, at some location, a tip internal radius of curvature that is a smallest radius of curvature of said concave surface,
wherein said tip cross-section can be enveloped by a minimum tip enveloping rectangle that is a smallest rectangle that can enclose said tip cross-section,
wherein said minimum tip enveloping rectangle has a tip section width dimension and a tip section height dimension and has a tip aspect ratio that is a ratio of said tip section width dimension to said tip section height dimension,
wherein said tip aspect ratio ranges from 1.0 to 3.5,
wherein said tip internal radius of curvature is between 2% and 40% of said body width dimension,
wherein said tip internal radius of curvature is approximately 0.05 to 6.25 times said tip thickness,
wherein when viewed from above said concave surface, said tip has a swept-back configuration, and wherein said tip has a distal edge having a suitable sharpness and hardness to cut a material of interest.

Further Comments

The blade of embodiments of the invention has been designed, first and foremost, to provide control to the surgeon so the blade is always moving where the surgeon wants it to go. The blade is designed so the surgeon can easily control the direction of cut and the depth of cut. In general, there tends to be a tradeoff between cutting speed and cutting control. The faster the cutting speed, the less control the surgeon has of the blade. It is possible that faster cutting blade designs can easily veer away from the intended line of cut or cut deeper than expected into the bone cement. If the blade is designed so that the cutting speed is significantly reduced, then the blade will cut too slowly to be effective, or will not cut at all. Finding a balance or "sweet spot" between blade control and cutting speed is the goal we seek in varying the different design parameters of the blade. We want to give the surgeon excellent control over the blade so that the surgeon can feel confident in not injuring the patient, while also providing sufficient cutting speed so the surgeon finds the blade to be much more effective at removing bone cement than using a hammer and chisel.

In embodiments of the invention, the powered handpiece can be powered by pneumatics or by electricity. Examples of a powered pneumatic handpiece are Palix Medical's Versa-Driver™ (described in U.S. Ser. No. 63/066,089, filed Aug. 14, 2020 and U.S. Ser. No. 17/402,511, filed Aug. 14, 2021) and Exactech's Acudriver®. An example of an electrically powered handpiece is DePuy Synthes' Kincise™.

The blade can be made from any strong material or combination of materials that can withstand the compressive or impact forces of the cutting action, along the proximal-distal direction of the blade 10, while maintaining a sharp cutting edge. Blade 10 may in general be made of a metal that is suitable for use in a surgical setting. Some examples are 300 and 400 series stainless steels, carbon fiber, ceramic, nickel titanium, etc. The blade, or in particular its cutting edge, may have a hardness greater than HRC 35. If present, a splash guard may be made of a polymer such as plastic or rubber. The chuck of the powered driving device, if present, may generally be made of a suitable metal, although other materials are also possible.

In an embodiment of the invention, the blade 10 may be formed starting with flat material and then deforming the flat material by bending, stamping etc.

In an embodiment of the invention, the cutting edge may be formed by grinding, or by other appropriate technique. The blade 10 could also be made by many other processes including forging, 3D printing, CNC machining, injection molding, or welding of two or more pieces of metal.

The grinding process can be performed by creating a three-dimensional profile on the face of a grinding wheel that matches the three-dimensional profile of the blade tip 20, so that when the grinding wheel contacts the blade it grinds the cutting edge evenly on all faces at the same time. The grinding wheel can then be moved relative to the blade, or the blade relative to the wheel, axially along a plane which creates an angle, equal to the Bevel Edge Angle "E", with the plane tangent to the convex portion of the blade tip. This will create a consistent Bevel Edge angle equal to angle "E" across the blade tip. An alternative means of grinding the blade tips is to use a CNC grinder or robotically controlled grinder that is able to produce grinding contours, allowing the grinding wheel to produce consistent Bevel Edge Angles.

It is also possible that a similar blade design could be used in a manual process with a hammer. If intended for manual use with a hammer, the blade could be provided with an impact surface for the hammer to strike, such as a handle. However, if used manually with a hammer, it could be expected that the speed of cut and ease of use would be less than the results with a powered handpiece.

It is further possible that edges of the tip 20 could be serrated.

Although the body of the blade is shown as being generally straight along the longitudinal direction of the body of the blade, it is also possible that, for a particular surgical situation, the body of the blade could be made with a shape, along its longitudinal direction, that is something other than straight, as shown in FIG. 15A and FIG. 15B.

It is also possible for the tip 20 to be along a different direction from the body 30, as can be seen in FIG. 16. The angle theta could be +/−10 degrees offset from the direction of the body 30.

In the various illustrations, the trough shaped cross-sections of the body and of the hub have been shown as having equal legs on each side of the longitudinal axis or plane of symmetry of the blade. However, it would also be possible that these legs could be unequal if desired. In such a situation, the minimum tip enveloping rectangle, or the minimum body enveloping rectangle, can simply be the smallest rectangle that can enclose the cross-section of the tip or body, even if the section is not fully symmetric.

Although embodiments of the invention have been described with respect to cutting bone cement, embodiments could also be used for cutting other material instead of or in addition to bone cement.

In general, any combination of disclosed features, components and methods described herein, that is physically possible, is intended to be within the scope of the claims.

All cited references are incorporated by reference herein.

Although embodiments have been disclosed, it is not desired to be limited thereby. Rather, the scope should be determined only by the appended claims.

We claim:

1. A blade for cutting, said blade comprising:
 a tip, said tip having a tip thickness measured perpendicular to a local surface of said blade; and
 a body, proceeding proximally from said tip, said body having a body width dimension;
 wherein said body and said tip both extend generally along a proximal-distal direction,
 wherein said tip is trough-shaped having a tip concave surface and an opposed tip convex surface,
 wherein said tip has a tip cross-section, taken perpendicular to said proximal-distal direction,
 wherein, said tip cross-section has a concave surface that has, at a location, a tip internal radius of curvature that is a smallest radius of curvature of said concave surface,
 wherein said tip cross-section can be enveloped by a minimum tip enveloping rectangle that is a smallest rectangle that can enclose said tip cross-section,
 wherein said minimum tip enveloping rectangle has a tip section width dimension and a tip section height dimension and has a tip aspect ratio that is a ratio of said tip section width dimension to said tip section height dimension,
 wherein said tip aspect ratio ranges from 1.0 to 3.5,
 wherein said tip internal radius of curvature is between 2% and 40% of said body width dimension, wherein said tip internal radius of curvature is approximately 0.05 to 6.25 times said tip thickness, wherein when viewed from above said concave surface, said tip has a swept-back configuration, and wherein said tip has a distal edge having a suitable sharpness and hardness to cut a material of interest.

2. The blade of claim 1, wherein said body has a body cross-section that comprises, in succession, a first straight leg body portion, a curved body portion continuous with said first straight leg body portion, and a second straight leg body portion continuous with said curved body portion.

3. The blade of claim 2, wherein said first straight leg body portion and said second straight leg body portion have an included angle therebetween that is between 40 degrees and 140 degrees.

4. The blade of claim 2, wherein said body cross-section comprises a curved shape, wherein a central portion of said body cross-section has a smaller local radius of curvature than a more-lateral portion of said body cross-section.

5. The blade of claim 1, wherein said tip internal radius of curvature is between 0.02 inch and 0.20 inch.

6. The blade of claim 1, wherein said swept-back configuration is such that, when viewed from above, a ratio tip length/tip width is between 0.1 and 2.0.

7. The blade of claim 1, wherein said swept-back configuration is such that, when viewed from above, a contour of said distal edge of said blade comprises a curved shape, and said curved shape is located between the following two boundaries:
  (a) an ellipse centered at a midplane of said blade and touching a distal-most point of said blade and having a sideways semi-axis that is half of a blade width dimension and a proximal-distal semi-axis that is one-quarter of said blade width dimension, and
  (b) an ellipse centered at a midplane of said blade and touching a distal-most point of said blade and having a sideways semi-axis that is half of said blade width dimension and a proximal-distal semi-axis that is said blade width dimension.

8. The blade of claim 1, wherein in plan view said tip has a shape that comprises at least one straight-line segment.

9. The blade of claim 1, wherein, if said body of said blade is unbent into a flat configuration, said tip has a frontal radius "Rf" of said tip, wherein said frontal radius Rf is between 0.1 inch and 0.5 inch.

10. The blade of claim 1, wherein said tip has a tapered cutting edge that is aligned with said convex surface of said tip or is offset from said convex surface of said tip by less than 10% of a body thickness, or is aligned with said concave surface of said tip or is located between said convex surface of said tip and said concave surface of said tip.

11. The blade of claim 1, wherein said distal edge of said tip has a cutting edge taper angle that may be approximately 25 degrees or may be between 5 degrees and 60 degrees.

12. The blade of claim 1, wherein said distal edge of said tip has a cutting edge radius of no more than 0.010 inch and said tip has a hardness of at least 35 HRC.

13. The blade of claim 1, wherein said tip has a distal edge taper having a taper angle and a slant dimension such that said taper angle varies as a function of position along an edge of said tip, or said slant dimension varies as a function of position along an edge of said tip, and/or said slant dimension being constant at a tip distal portion of said tip and gradually decreasing in a proximal direction therefrom.

14. The blade of claim 1, wherein said blade comprises metal and has a thickness suitable so that said blade can withstand a compressive force or impact force, along said proximal-distal direction, of at least 10 N without buckling.

15. The blade of claim 1, wherein said body and said tip are symmetric about a plane that proceeds along said proximal-distal direction midway between first and second side edges of said body.

16. The blade of claim 1, wherein said blade further comprises, proximally of said body, a transition region connected to said body, and further comprises, proximally of said transition region, a hub that is connected to said transition region, wherein said body and said transition region and said hub all have cross-sectional shapes that are different from each other.

17. The blade of claim 16, wherein said hub is suitable to be gripped by a pneumatically driven or electrically driven power instrument or is suitable to be impacted by a hammer.

18. The blade of claim 16, wherein, in a cross-section of said hub taken perpendicular to said proximal-distal direction, said hub has a hub cross-section, and wherein said hub cross-section can be enveloped by a minimum hub enveloping rectangle that is a smallest rectangle that can enclose said hub cross-section, wherein said minimum hub enveloping rectangle has a hub width dimension and a hub height dimension and has a hub aspect ratio that is a ratio of said hub width dimension to said hub height dimension, wherein said hub aspect ratio ranges from 0.1 to 10, wherein said hub aspect ratio is different from said tip aspect ratio.

19. The blade of claim 1, wherein said body is trough-shaped having a body concave surface and having a body convex surface that is opposed to said body concave surface, said body concave surface and said tip concave surface being continuous with each other, said body convex surface and said tip convex surface being continuous with each other.

20. A method of cutting bone cement, said method comprising providing the blade of claim 1, and causing said blade to repeatedly strike said bone cement suitably to cut or remove said bone cement.

\* \* \* \* \*